US007265368B2

(12) United States Patent
Martin, III

(10) Patent No.: US 7,265,368 B2
(45) Date of Patent: Sep. 4, 2007

(54) ION OPTICAL MOUNTING ASSEMBLIES

(75) Inventor: Roy E. Martin, III, Worcester, MA (US)

(73) Assignees: Applera Corporation, Framingham, MA (US); MDS, Inc., Ontatario (CA)

( * ) Notice: Subject to any disclaimer, the term of this patent is extended or adjusted under 35 U.S.C. 154(b) by 279 days.

(21) Appl. No.: 11/129,022

(22) Filed: May 13, 2005

(65) Prior Publication Data

US 2006/0255294 A1 Nov. 16, 2006

(51) Int. Cl.
*A61N 5/00* (2006.01)
*G21G 5/00* (2006.01)

(52) U.S. Cl. .................. 250/492.3; 250/288; 250/287; 250/281; 250/282; 409/219; 385/137; 385/14

(58) Field of Classification Search ..................... None
See application file for complete search history.

(56) References Cited

U.S. PATENT DOCUMENTS 6,797,948 B1 * 9/2004 Wang ......................... 250/292
6,858,839 B1 2/2005 Anderson et al.

* cited by examiner

*Primary Examiner*—Jack I. Berman
*Assistant Examiner*—Zia R. Hashmi
(74) *Attorney, Agent, or Firm*—Michael J. Bastian; Choate Hall & Stewart, LLP

(57) ABSTRACT

In various embodiments, provided are ion optical assemblies, and systems for mounting and aligning ion optic components. In various embodiments, the present teachings provide ion optical assemblies with features that facilitate the alignment of ion optical elements. In various embodiments, the alignment of the ion optical elements by compressing them with securing members, as described in the present teachings, can simplify the alignment and assembly of ion optical elements. In the present teachings, no torque pattern is required to compress and align the ion optical elements. In various embodiments, the present teachings provide systems for mounting and aligning ion optic components that facilitate their alignment.

20 Claims, 19 Drawing Sheets

ION OPTICAL MOUNTING ASSEMBLIES

INTRODUCTION

The development of matrix-assisted laser desorption/ionization ("MALDI") techniques has greatly increased the range of biomolecules that can be studied with mass analyzers. MALDI techniques allow normally nonvolatile molecules to be ionized to produce intact molecular ions in a gas phase that are suitable for analysis. One class of MALDI instrument, which have found particular use in the study of biomolecules, are MALDI tandem time-of-flight mass spectrometers, referred to as MALDI-TOF MS/MS instruments hereafter.

A traditional tandem mass spectrometer (MS/MS) instrument uses multiple mass separators in series. An MS/MS instrument can be use, for example, to determine structural information, such as, e.g., the sequence of a protein. Traditional MS/MS techniques use the first mass separator (often referred to as the first dimension of mass spectrometry) to transmit molecular ions in a selected mass-to-charge (m/z) range (often referred to as "the parent ions" or "the precursor ions") to an ion fragmentor (e.g., a collision cell, photodissociation region, etc.) to produce fragment ions (often referred to as "daughter ions") of which a mass spectrum is obtained using a second mass separator (often referred to as the second dimension of mass spectrometry).

Time-of-flight (TOF) mass spectrometers distinguish ions on the basis of the ratio of the mass of the ion to the charge of the ion, often abbreviated as m/z. Traditional TOF techniques rely upon the fact that ions of different mass-to-charge ratios (m/z) achieve different velocities if they are all exposed to the same electrical field; and as a result, the time it takes an ion to reach the detector (called the ion arrival time or time of flight) is representative of the ion mass. In theory, each ion of a given mass-to-charge ratio should have a unique arrival time. As a result, a mixture of ions of different mass should produce a spectrum of arrival time signals each corresponding to a different ion mass. Such spectra are commonly referred to as arrival time spectra or simply, mass spectra. In practice, however, achieving accurate results is not easy, and the greater the accuracy required in the analysis, the more difficult the task.

Several operational configurations of MALDI mass spectrometers which have found particular use in the study of biomolecules, are linear time-of-flight ("TOF") mass spectrometers, reflectron TOF mass spectrometers, and tandem TOF mass spectrometers referred to as MS/MS TOF instruments hereafter. Each of these configurations has its own advantages and disadvantages depending, e.g., on the biomolecules of interest, the nature of the study, etc. Accordingly, commercial instruments exist which are configured so that an investigator can switch from one operational mode (linear TOF, reflectron TOF, and MS/MS TOF) to another.

Although instruments exist where the mode of operation can be switched, the instrument configurations and operational conditions that provide good resolution and sensitivity for one mode of operation (e.g., linear TOF, reflectron TOF, and MS/MS TOF) can significantly decrease the resolution and sensitivity for other operational modes. As a result, conventional instruments often must comprise the resolution and/or sensitivity of at least one of these three operational modes to provide an instrument that has acceptable resolution and sensitivity in all three modes.

In many biomolecule studies (such as, e.g., proteomics studies) that employ mass analyzers the biomolecule masses of interest can readily span two or more orders of magnitude.

In addition, in many biological studies there is a limited amount of sample available for study (such as, e.g., rare proteins, forensic samples, archeological samples).

In a tandem mass spectrometer (MS/MS), it is also generally desirable to control the collision energy of the ions prior to the ions entering the ion fragmentor, e.g., a collision cell. Typically, this is done in a TOF/TOF tandem mass spectrometer by first accelerating the ions from the first TOF region (first dimension of MS) to an initial energy and then decelerating the ions to the desired collision energy by adjusting the electrical potential on the collision cell entrance. In general, it is simple to optimize an ion optical system for a single collision energy that provides good focusing into the second TOF region following the collision cell, however, it is considerably more difficult to provide an ion optical system that provides good focusing into the second TOF region across a range of collision energies, without compromising ion transmission efficiency and thereby instrument sensitivity.

MALDI-TOF MS/MS instruments can also be very complex machines requiring the accurate alignment and interaction of myriad components for useful operation. Mass spectrometry requires ion optics to focus, accelerate, decelerate, steer and select ions. Misalignment of theses and non-uniformity in their electrical fields can significantly degrade the performance of a mass spectrometry instrument. The ion optical elements are positively positioned in the X, Y and Z directions with respect to each other and other components of the instrument. Once positioned, subsequent movements of the ion optical elements can significantly degrade instrument performance. For example, if an element moves out of alignment after an instrument has been tuned, the instrument's mass accuracy, sensitivity and resolution can be adversely affected.

Traditional ion optics stack assemblies have used assembly jigs, where possible, to position the ion optical elements followed by securing the optics in place with threaded fasteners. For example, a series of optical elements is stacked up, some using assembly jigs and some having self-aligning features, an end plate is bolted over the end of the stack, and the bolts tightened to compress the optical elements with the end plate and secure the stack. In addition, such traditional methods of assembly often require the assembler to tighten the bolts in both a specific pattern and with specific torques to properly align the ion optical elements, e.g. without warping. Such procedures, however, can be time-consuming and can require a skilled assembler to perform. In addition, as the alignment tolerances of instruments decrease (e.g., to improve sensitivity, decrease instrument size, etc.) misalignment errors become less and less noticeable to the naked eye and harder to detect by the less skilled assembler.

SUMMARY

The present teachings relate to MALDI-TOF instruments, instrument components, and methods of operation thereof. In various aspects, the MALDI-TOF instrument can serve and be operated as a MS/MS instrument. In various embodiments, provided are MALDI-TOF instruments, and methods of operating one or more components of a MALDI-TOF instrument, that facilitate one or more of increasing sensitivity, increasing resolution, increasing dynamic mass range, increasing sample support throughput, and decreasing operational downtime.

In various aspects, the present teachings provide systems for providing sample ions, methods for providing sample ions, sample support handling mechanisms, ion sources methods for focusing ions from a delayed extraction ion source, methods for operating a time-of-flight mass analyzer, In various aspects, the present teaching provide mass analyzer systems comprising one or more of the systems for providing sample ions, methods for providing sample ions, sample support handling mechanisms, ion sources, methods for focusing ions from a delayed extraction ion source, methods for operating a time-of-flight mass analyzer, methods for focusing ions for an ion fragmentor, methods for operating an ion optics assembly, ion optical assemblies, and systems for mounting and aligning ion optic components of the present teachings.

Sample Handling Mechanisms

In various aspects, the present teachings relate to sample support handling mechanisms for a mass analyzer system. In various embodiments, the sample support comprises a plate, e.g., a 3.4"×5" plate, a microtiter sized MALDI plate, etc. The sample support handling mechanisms of the present teachings comprising a sample support transfer mechanism portion and a sample support changing mechanism portion, where the sample support changing mechanism portion is disposed in a vacuum lock chamber.

In various embodiments, the sample support transfer mechanism comprises a base member having a substantially planar front face and a left arm and a right arm which extend from the base member in a direction X substantially perpendicular to the front face and are spaced apart from each other in a direction Y substantially parallel to the front face a distance sufficient to fit a sample support between them. The left arm and the right arm each having a bearing support structure. In various embodiments, the left arm and right arm each have a retention projection extending in the Y direction towards the other arm a distance smaller than the distance between the arms.

In various embodiments, a sample support is retained within a frame member. It is to be understood that in the present teachings that the descriptions of handling (e.g., capture, engagement, disengagement, etc.) and registration of a sample support are equally applicable to a sample support retained in a frame member where, e.g., are the various structures of the sample transfer and changing mechanism are in direct contact with the frame member and do not necessarily directly contact the sample support retained therein.

In various embodiments, a sample support is retained on a frame such as described in U.S. Pat. Nos. 6,844,545 and 6,825,478, the entire contents of which are hereby incorporated by reference. In various embodiments, a frame member has a perimeter ridge portion, which, for example, can engage (e.g., slip over) at least a portion of the perimeter of capture mechanism of a sample changing mechanism of the present teachings to facilitate, e.g., retaining a sample support in an unload region of the changing mechanism.

The sample support transfer mechanism further comprises an engagement member situated between the left and the right arms, where in a first position the engagement member is configured to urge a front end of a sample support into registration with the front face of the base member and to urge the front end of the sample support into registration in a direction Z (the direction Z being substantially perpendicular to both the X and Y directions), and the left and right bearing support structures are configured in a first position to urge a back end of a sample support into registration in a direction Z.

In various embodiments, the sample support transfer mechanism comprises three cam structures, a left cam structure, a right cam structure, and a central cam structure disposed between the left and right cam structures. Between the left and central cam structures is a sample support loading region and between the central and right cam structures is a sample support unloading region.

The sample support loading region comprises a first disengagement member capable of urging the engagement member to a second position and a registration member capable of urging a sample support against the front face and the left arm. The left cam structure being capable of (a) slideably engaging the left arm bearing support structure to urge the left arm bearing support structure to a second position; and (b) engaging the registration member and causing the registration member to urge a sample support against the front face and the left arm. The central cam structure being capable of slideably engaging the right arm bearing support structure to urge the right arm bearing support structure to a second position, so when the engagement member, the left arm bearing support structure and the right arm bearing support structure are in their respective second positions, the sample support transfer mechanism is capable of engaging a sample support between the left and right arms of the sample support transfer mechanism.

The sample support unloading region comprises a second disengagement member capable of urging the engagement member to a third position and a sample support capture mechanism configured to retain a sample support in the sample support unloading region after it is disengaged from the sample support transfer mechanism. The central cam structure being capable of slideably engaging the left arm bearing support structure to urge the left arm bearing support structure to a third position and the right cam structure capable of slideably engaging the right arm bearing support structure to urge the right arm bearing support structure to a third position, so when the engagement member, the left arm bearing support structure and the right arm bearing support structure are in their respective third positions, the sample support transfer mechanism is capable of disengaging a sample support from between the left right arms of the sample support transfer mechanism.

In various embodiments, the engagement member of the sample transfer handling mechanism comprises a latch attached to the base member. In various embodiments, the latch comprises a roller which contacts the second disengagement member and allows the sample support to slowly disengage from the sample support transfer mechanism.

In various embodiments, the sample support transfer mechanism comprises a frame having an electrically conductive surface. In various embodiments, such a frame facilitating the reduction of electrical field line discontinuity at and/or near the edges of a sample support.

In various embodiments, the sample support transfer mechanism transfers a sample support from a region of low vacuum (e.g., the vacuum lock chamber) to a region of higher vacuum (e.g., a sample chamber). In various embodiments, the sample chamber is configured to achieve a pressure of less than or equal to about $10^{-6}$ Torr. In various embodiments, the sample chamber is configured to achieve a pressure of less than or equal to about $10^{-7}$ Torr. As such, in various embodiments, the sample support transfer mechanism is made of vacuum compatible materials.

In various embodiments, the sample support handling mechanism facilitates providing consistent positioning of a sample support for subsequent ion generation by MALDI. In various embodiments, the sample support handling mechanism is configured such that a sample support is registered to a position in the sample transfer mechanism to: (a) within about ±0.005" in the Z direction; (b) within about ±0.01" in the X direction; (c) within about ±0.01" in the Y direction; (d) or combinations thereof. In various embodiments, the sample support handling mechanism is configured such that a sample support is registered to a position in the sample transfer mechanism to: (a) within about ±0.002" in the Z direction; (b) within about ±0.005" in the X direction; (c) within about ±0.005" in the Y direction; (d) or combinations thereof.

In various aspects, the present teachings provide a system for providing sample ions comprising a vacuum lock chamber and a sample chamber connected to the vacuum lock chamber, where disposed in the vacuum lock chamber is a sample support changing mechanism and disposed in the sample chamber is a sample support transfer mechanism. The sample support transfer mechanism being configured to extract a sample support from a loading region of the sample support changing mechanism such that the sample support is registered in the sample support transfer mechanism. In various embodiments, the sample support is registered to within about ±0.005" in a Z direction, to within about ±0.01" in a X direction, and to within about ±0.01" in a Y direction, wherein the X, Y and Z directions are mutually orthogonal. In various embodiments, the sample support is registered to within about ±0.002" in a Z direction, to within about ±0.005" in a X direction, and to within about ±0.005" in a Y direction, wherein the X, Y and Z directions are mutually orthogonal. In various embodiments, the sample support is registered within a frame in the sample support transfer mechanism. The sample support transfer mechanism also being mounted on a multiaxis translation stage such that the sample support can be translated to a position where sample ions can be generated by laser irradiation of a sample on the surface of the sample support while said sample support is held in the sample support transfer mechanism and said sample ions extracted into a mass analyzer system in a direction substantially perpendicular to the surface of the sample support. In various embodiments, the Z direction being substantially perpendicular to the surface of the sample support.

In various embodiments, sample ions are extracted in a direction substantially perpendicular to the surface of the sample support along a first ion optical axis which is substantially coaxial with the laser irradiation. For example, in various embodiments, a system for providing sample ions is configured such that sample ions are extracted from the sample chamber along a direction that is substantially coaxial with the Poynting vector of the pulse of laser energy striking the sample which generated the sample ions. In various embodiments, the first ion optical axis forms an angle that is within about 5 degrees or less of the normal of the sample surface. In various embodiments, the first ion optical axis forms an angle that is within about 1 degree or less of the normal of the sample surface.

In various embodiments, a frame member has an electrically conductive surface, at least on the surface facing the ion extraction direction. In various embodiments, such a frame facilitates reducing electrical field line discontinuities at and/or near the edges of a sample support.

In various aspects, the present teachings provide methods for providing sample ions for mass analysis comprising: supporting a plurality of samples on a surface of a sample support; providing a vacuum lock chamber having a region for loading a sample support and a region for unloading a sample support; and providing a sample chamber having a sample transfer mechanism disposed therein. The methods extract the sample support disposed in the region for loading with the sample transfer mechanism such that the sample support is registered in the sample support transfer mechanism. In various embodiments, the sample support is registered within a frame in the sample support transfer mechanism. In various embodiments, the sample support is registered to within about ±0.005" in a Z direction, to within about ±0.01" in a X direction, and to within about ±0.01" in a Y direction, wherein the X, Y and Z directions are mutually orthogonal and the direction Z is substantially perpendicular to the surface of the sample support. In various embodiments, the sample support is registered to within about ±0.002" in a Z direction, to within about ±0.005" in a X direction, and to within about ±0.005" in a Y direction, wherein the X, Y and Z directions are mutually orthogonal. The sample support is translated to a first position within the sample chamber where a first sample on the surface of the sample support is irradiated with a pulse of energy to form a first group of sample ions while the sample support is being held by the sample transfer mechanism and at least a portion of the first group of sample ions is extracted in the Z direction. The sample support is then translated to a second position within the sample chamber where a second sample on the surface of the sample support is irradiated with a with a pulse of energy to form a second group of sample ions while the sample support is being held by the sample transfer mechanism and at least a portion of the second group of sample ions is extracted in the Z direction. Further samples can be analyzed on the sample support prior to the sample support being placed by the sample support transfer mechanism in the region for unloading a sample support. The methods continue with repeating the steps of extracting a sample support followed by the steps of translating, irradiating and extracting for at least two samples.

In various embodiments, at least one of the steps of irradiating a sample with a pulse of energy comprises irradiating the sample at an irradiation angle that is within 5 degrees or less of the normal of the surface of the sample support to form sample ions by matrix-assisted laser desorption/ionization. In various embodiments, at least one of steps irradiating a sample with a pulse of energy comprises irradiating the sample at an irradiation angle that is within 1 degree or less of the normal of the surface of the sample support to form sample ions by matrix-assisted laser desorption/ionization.

In various embodiments, at least one of the steps of extracting at least a portion of the sample ions comprises extracting sample ions in the Z direction along a first ion optical axis, wherein the first ion optical axis is substantially coaxial with the pulse of energy.

Ion Sources

In various aspects, the present teachings relate to ion sources for TOF instruments, and methods of operation thereof. In various embodiments, the present teachings relate to matrix-assisted laser desorption/ionization (MALDI) ion sources and methods of MALDI ion source operation, for use with mass analyzers. In various aspects, provided are ion sources and methods of operation thereof that facilitate increasing one or more of sensitivity and resolution of a TOF mass analyzer configured for multiple modes of operation.

In a general purpose MALDI TOF mass spectrometer, it is desirable to change the position of the velocity space focus plane of the ion source such that optimal resolution is attained for different modes of operation, i.e., linear, reflector (ion mirror), and precursor (parent ion) selection for MS/MS. A typical two-stage Wiley McLaren type source employing delayed extraction can be designed to provide ideal focusing for any singular mode of operation. However, it is more difficult to design a singular geometry that provides optimized performance in more than one mode of operation without sacrificing performance elsewhere. In particular, to optimize the source for a focal plane close to the source, such as can be required for timed ion selection for MS/MS, the spatial focusing of the beam (in x, y) is degraded to the point where significant portions of the ion beam are not transmitted through critical apertures; and hence, a substantial loss of instrument sensitivity is observed. The present teachings, in various embodiments, provide novel three-stage ion sources that allow for an adjustable velocity space focus plane and improved x,y spatial focus characteristics of the ion beam compared to conventional two-stage ion sources. In various embodiments, the ion source facilitates compensating for the spread in ion arrival times due to initial ion velocity without substantially degrading the radial spatial focusing of the ions.

The skilled artisan will recognize that the concepts described herein using the terms "velocity space focus" and "x,y spatial focus" can be described using different terms. As delayed extraction can be used to bring ions with different initial velocities, but the same m/z value, to a particular plane in space at substantially the same time, this process has been referred to by several terms in the art including, "time focusing" and "space focusing," "velocity focusing" and "time-lag focusing." In addition, for example, the terms "space focus," "space focus plane," "space focal plane," "time focus," "velocity focusing" and "time focus plane" have all been used in the art to refer to one or more of what are referred to herein as the velocity space focus plane. Unfortunately, the terms "time focusing," "temporal focusing," "space focus," "space focus plane," "space focal plane," "time focus" and "time focus plane" have also been used in the art of time-of-flight mass spectrometry to describe processes that are fundamentally different from the velocity space focusing of an ion source using delayed extraction. As x,y spatial focusing can narrow the diameter of an ion beam in a direction perpendicular to its primary propagation direction, z, this process has also been referred to in the art by the term "radial focusing." However, the terms "spatial focusing" and "radial focusing" have also been used in the art of time-of-flight mass spectrometry to describe processes that are fundamentally different from the x,y spatial focusing of the present teachings. Accordingly, given the complex usage of terminology found in the mass spectrometry art, the terms "velocity space focus" and "x,y spatial focus" used herein were chosen for conciseness and consistency in explanation only and should not be construed out of the context of the present teachings to limit the subject matter described in any way.

In various aspects, a three-stage ion source of the present teachings comprises a first electrode spaced apart from a sample support having a sample surface, a second electrode spaced apart from the first electrode in a direction opposite the sample support, and a third electrode spaced apart from the second electrode in a direction opposite the first electrode. The sample support, first, second and third electrodes are electrically coupled to a power source which is adapted to: (a) apply a first potential to the sample surface and a second potential to at least one of the first electrode and the second electrode to establish a non-extracting electric field at a first predetermined time substantially prior to striking a sample on the sample surface with a pulse of energy to form sample ions, the non-extracting electrical field substantially not accelerating sample ions in a direction away from the sample surface; (b) change the electrical potential of at least one of the sample surface and the first electrode to establish a first extraction electric field at a second predetermined time subsequent to the first predetermined time, the first extraction electric field accelerating sample ions in a first direction away from the sample surface; and (c) apply a third potential to the second electrode to focus ions in a direction substantially perpendicular to the first direction.

In various embodiments, the non-extracting electrical field can be a retardation electrical field which retards the motion of sample ions in a direction away from the sample surface. In various embodiments, the non-extracting electrical field can be a substantially zero electrical field, e.g., a substantially electrical field free region is established. A substantially zero electrical field can be established, e.g., when the first potential and the second potential are substantially equal.

In various embodiments, the first direction is substantially coaxial with the pulse of energy. For example, in various embodiments, sample ions are extracted along a first direction which is substantially coaxial with the Poynting vector of the pulse of energy striking the sample which generated the sample ions. In various embodiments, the first direction forms an angle that is within about 5 degrees or less of the normal of the sample surface. In various embodiments, the first direction forms an angle that is within about 1 degree or less of the normal of the sample surface Application of a potential difference between the sample support and first electrode that accelerates sample ions away from the sample surface can be delayed by a predetermined time subsequent to generation of the pulse of laser energy to perform, for example, delayed extraction. In some embodiments, delayed extraction is performed to provide time-lag focusing to correct for the initial sample ion velocity distribution, for example, as described in U.S. Pat. No. 5,625,184 filed May 19, 1995, and issued Apr. 29, 1997; U.S. Pat. No. 5,627,369, filed Jun. 7, 1995, and issued May 6, 1997; U.S. Pat. No. 6,002,127 filed Apr. 10, 1998, and issued Dec. 14, 1999; U.S. Pat. No. 6,541,765 filed May 29, 1998, and issued Apr. 1, 2003; U.S. Pat. No. 6,057,543, filed Jul. 13, 1999, and issued May 2, 2000; and U.S. Pat. No. 6,281,493 filed Mar. 16, 2000, and issued Aug. 28, 2001; and U.S. application Ser. No. 10/308,889 filed Dec. 3, 2002; the entire contents of all of which are herein incorporated by reference. In other embodiments, extraction can be performed to correct for the initial sample ion spatial distribution, for example, as described in W. C. Wiley and I. H. McLaren, *Time-of-Flight Mass Spectrometer with Improved Resolution*, Review of Scientific Instruments, Vol. 26, No. 12, pages 1150-1157, (December 1955), the entire contents of which are herein incorporated by reference.

In various embodiments of operation, a sample is irradiated with a pulse of laser energy at an irradiation angle to produce sample ions by MALDI. After any previous sample ion extraction and during the irradiation of the sample with the pulse of laser energy, the power source applies a first potential to the sample support and a second potential to at least one of the first electrode and the second electrode to establish a first electrical field at a first predetermined time relative to the generation of the pulse of energy, the first electrical field substantially not accelerating sample ions in a direction away from the sample support. In some embodiments, the first potential is more negative than the second potential when measuring positive sample ions, and the first potential is less negative than the second potential when measuring negative sample ions, to thereby produce a retarding electrical field prior to sample ion extraction. In various embodiments, the first electrical field can be a substantially zero electrical field, e.g., a substantially electrical field free region is established. A substantially zero electrical field can be established, e.g., when the first potential and the second potential are substantially equal.

In various embodiments, at a second predetermined time subsequent to the generation of the pulse of laser energy, the power source changes a potential on at least one of the sample support and the first electrode to establish a second electrical field that accelerates sample ions away from the sample support to extract the sample ions and applies a third potential to the second electrode to provide x,y spatial focusing.

A wide variety of structures can be used to control the timing of the generation of the potentials. For example, a photodetector can be used to detect the pulse of laser energy and generate an electrical signal synchronously timed to the pulse of energy. A delay generator with an input responsive to the synchronously timed signal can be used to provide an output electrical signal, delayed by a predetermined time with respect to the synchronously timed signal, for the power source to trigger or control the application of the various potentials.

In various embodiments, a three-stage ion source of the present teachings is configured to extract sample ions in a direction substantially normal to the sample surface and includes an optical system configured to irradiate a sample on the sample surface of a sample support with a pulse of laser energy at an angle substantially normal to the sample surface. In various embodiments, the first electrode and second electrode, each have an aperture. The first and second electrodes are in some embodiments arranged such that a first ion optical axis (defined by the line between the center of the aperture in the first electrode and the center of the aperture in the second electrode) intersects the sample surface at an angle substantially normal of the sample surface. In various embodiments, the optical system is configured to substantially coaxially align the pulse of laser energy with the first ion optical axis.

In various aspects, three-stage ion sources which facilitate reducing material deposition on electrodes in the ion beam path are provided. Reducing material deposition on electrodes in the ion beam path can facilitate, for example, increased mass analyzer sensitivity, resolution, or both, and facilitate decreasing the operational downtime of a mass analyzer.

In one aspect, a three-stage ion source can be provided where one or more of the elements of the ion source are connected to a heater system; and a temperature-controlled surface is disposed substantially around at least a portion of the three-stage ion source. Suitable heater systems include, but are not limited to, resistive heaters and radiative heaters. In some embodiments, the heater system can raise the temperature of one or more of the elements in the ion source to a temperature sufficient to desorb matrix material. In various embodiments, the heater system includes a heater capable of heating one or more of the elements in the ion source to a temperature greater than about 70° C.

The temperature of the temperature-controlled surface can be actively controlled, for example, by a heating/cooling unit, or passively controlled, such as, for example, by the thermal mass of the temperature-controlled surface, placing the temperature-controlled surface in thermal contact with a heat sink, or combinations thereof.

In other various aspects, three-stage ion sources for, and methods of, providing sample ions for mass analysis are provided. In various embodiments, the ion sources and methods are suitable for providing sample ions for mass analysis by time-of-flight mass spectrometry, including, but not limited to, multi-dimensional mass spectrometry. Examples of suitable time-of-flight mass analysis systems and methods are described, for example, in U.S. Pat. No. 6,348,688, filed Jan. 19, 1999, and issued Feb. 19, 2002; U.S. application Ser. No. 10/023,203 filed Dec. 17, 2001; U.S. application Ser. No. 10/198,371 filed Jul. 18, 2002; and U.S. application Ser. No. 10/327,971 filed Dec. 20, 2002; the entire contents of all of which are herein incorporated by reference.

In various aspects, the present teachings provide methods for focusing ions from an ion source. In various embodiments, the ion source comprises a delayed extraction ion source. In various embodiments, the methods focus ions from an ion source having a sample support, a first electrode spaced apart from the sample support, a second electrode spaced apart from the first electrode in a direction opposite the sample support holder, and a third electrode spaced apart from the second electrode in a direction opposite the first electrode. Samples for ionization are disposed on a sample surface of the sample support and the energy of the ions can be established by an electrical potential difference between the sample surface and the third electrode. In various embodiments, ions are focused by selecting the position of a time-focus plane of the ion source in a direction z by application of an electrical potential difference between the sample surface and the first electrode, where this potential difference is established by applying a first electrical potential to the sample surface and a second electrical potential to the first electrode; and focusing ions in a direction substantially perpendicular to the direction z by application of a third electrical potential to the second electrode.

In various aspects, the present teachings provide methods for operating a time-of-flight (TOF) mass analyzer having two or more modes of operation, and an ion source. Examples of modes of operation include, but are not limited to, linear TOF, reflectron TOF, and MS/MS TOF. In various embodiments, the ion source having a sample support, a first electrode spaced apart from the sample support, a second electrode spaced apart from the first electrode in a direction opposite the sample support holder, and a third electrode spaced apart from the second electrode in a direction opposite the first electrode.

In various embodiments, the methods for operating of a TOF mass analyzer having two or more modes of operation comprise: (a) establishing an ion energy by selecting an electrical potential difference between the sample surface and the third electrode; (b) selecting for a first mode of operation the position of a time-focus plane in a direction z by applying a first electrical potential to the sample surface and a second electrical potential to the first electrode; and (c) focusing for the first mode of operation ions in a direction substantially perpendicular to the direction z by applying a third electrical potential to the second electrode. In various embodiments, the methods further comprise: (d) changing the mode of operation of the time-of-flight mass analyzer to a second mode of operation; (e) selecting for the second mode of operation the position of a time-focus plane in a direction z by changing the electrical potential applied to the first electrode; and (f) focusing for the second mode of operation ions in a direction substantially perpendicular to the direction z by changing the electrical potential applied to the second electrode. In various embodiments, the time-focus plane is a time-focus plane of a delayed extraction ion source.

In various embodiments of focusing ions from an ion source, of operating a time-of-flight (TOF) mass analyzer having two or more modes of operation, or combinations thereof, sample ions are produced by irradiating a sample with a pulse of laser energy where the irradiation angle is substantially normal to the sample surface. In some embodiments, the sample ions so produced are extracted in an extraction direction that is substantially normal to the sample surface and the pulse of laser energy is substantially aligned with the extraction direction. In various embodiments, sample ions are produced by irradiating a sample with a pulse of laser energy where the Poynting vector of the pulse of energy intersecting the sample surface is substantially coaxial with the ion extraction direction. For example, in various embodiments, sample ions are extracted along a first ion optical axis in a direction substantially normal to the sample surface and the pulse of energy is substantially coincident with the first ion optical axis.

For example, in various embodiments, the methods comprise irradiating a sample on the sample surface with a pulse of energy at an irradiation angle that is within 1 degree or less of the normal of the sample support surface to form sample ions by matrix-assisted laser desorption/ionization and extracting sample ions along a first ion optical axis in a direction substantially normal to the sample support surface by application of an electrical potential difference between the sample support surface and the first electrode at a predetermined time. In various embodiments, the first ion optical axis is substantially coaxial with the pulse of energy.

Ion Optics

In various aspects, the present teachings provide methods for focusing ions for an ion fragmentor and methods for operating an ion optical assembly comprising an ion fragmentor. In various embodiments, the present teachings provide methods that substantially maintain the position of the focal point of the an incoming ion beam over a wide range of collision energies, and thereby provide a collimated ion beam for a collision cell over a wide range of energies. In various embodiments, the present teachings provide methods that facilitate decreasing ion transmission losses over a wide range of collision energies.

In various aspects, an ion optics assembly of the methods comprises a first ion lens disposed between a retarding lens and an entrance to a collision cell. In various embodiments, the retarding lens and first ion lens comprise multiple elements, and can share elements. For example, in various embodiments, the retarding lens comprises a first electrode, a second electrode and a third electrode; and the first ion lens comprises the third electrode, a fourth electrode and a fifth electrode. In various embodiments, sample ions are substantially focused to a focal point between the third electrode and the fourth electrode to form a substantially collimated ion beam after the focal point and before the entrance to the collision cell.

In various aspects, the present teachings provide methods for operating an ion optics assembly comprising a first ion lens disposed between a retarding lens and an entrance to a collision cell, comprising the steps of: focusing sample ions at a focal point within the first ion lens a distance F from an entrance to the retarding lens and forming a substantially collimated ion beam of sample ions at a first collision energy of the sample ions with respect to a neutral gas in a collision cell; and maintaining the focal point substantially at the distance F for collision energies different from the first collision energy by substantially maintaining the electrical potential on the retarding ion lens and changing an electrical potential on the first ion lens.

In various aspects, the present teachings provide methods for focusing ions for an ion fragmentor; the methods using an ion optics assembly comprising a first ion lens disposed between a retarding lens and an entrance to an ion fragmentor. In various embodiments, the methods apply a decelerating electrical potential to the retarding lens, apply an accelerating electrical potential difference between the retarding lens and the first ion lens; and apply a decelerating electrical potential difference between the first ion lens and the entrance to the collision cell. In various embodiments, sample ions are substantially focused to a focal point within the first ion lens, e.g., to form a substantially collimated ion beam after the focal point and before the entrance to the collision cell. In various embodiments, the position of this focal point is maintained for different collision energies by changing the accelerating electrical potential difference between the retarding lens and the first ion lens while substantially maintaining the decelerating electrical potential applied to the retarding lens.

In various embodiments, methods of the present teachings for operating an ion optics assembly comprising a first ion lens disposed between a retarding lens and an entrance to a collision cell, comprise: (a) at a first collision energy substantially focusing sample ions to a focal point in the first ion lens and forming after the focal point in the first ion lens and before the entrance to the collision cell a substantially collimated ion beam of sample ions by: (i) establishing a decelerating electrical field to decelerate sample ions entering the retarding lens by applying a first electrical potential to an electrode of the retarding lens; (ii) establishing an accelerating electrical field between the retarding lens and the first ion lens to accelerate sample ions from the retarding lens and into the first ion lens by applying a second electrical potential to an electrode of the first ion lens; and (iii) establishing a decelerating electrical field between the first ion lens and the entrance of the collision cell to decelerate sample ions from the first ion lens by applying a third electrical potential to the entrance of the collision cell. The methods proceed with (b) changing the first collision energy to a second collision energy different from the first collision energy. Sample ions for are then (c) at the second collision energy substantially focusing sample ions to the focal point in the first ion lens and forming after the focal point in the first ion lens and before the entrance to the collision cell a substantially collimated ion beam of sample ions by: (i) establishing a decelerating electrical field to decelerate sample ion entering the retarding lens by applying a fourth electrical potential to an electrode of the retarding lens, the fourth electrical potential being substantially equal to the first electrical potential; (ii) establishing an accelerating electrical field between the retarding lens and the first ion lens to accelerate sample ions from the retarding lens and into the first ion lens by applying a fifth electrical potential to an electrode of the first ion lens; and (iii) establishing a decelerating electrical field between the first ion lens and the entrance of the collision cell to decelerate sample ions from the first ion lens by applying a sixth electrical potential to the entrance of the collision cell.

In various embodiments, sample ions are substantially focused to a focal point a distance F from an entrance to the retarding lens. In various embodiments when the difference between the first collision energy and the second collision energy is less than about 5000 electron volts, the distance F varies within less than about: (a) ±4%; (b) ±2%; and/or (c) ±1%. In various embodiments, the fourth electrical potential is within about ±5% or less of the first electrical potential. For example, in various embodiments, the fourth electrical potential is within about ±2.5% or less of the first electrical potential.

Ion Optics Assemblies

In various aspects, the present teachings provide ion optical assemblies with features that facilitate the alignment of ion optical elements. In various embodiments, provided are ion optical assemblies comprising a first plurality of ion optical elements disposed between a front member and a front side of a mounting body. The front member is attached to the mounting body by at least one attachment member and the front member has a threaded opening configured to accept a threaded surface of a front securing member. The threaded opening of the front member is configured such that when the threaded surface of the front securing member is engaged in the threaded opening of the front member, a contact face of the front securing member can contact an ion optical element of the first plurality and apply a compressive force against the first plurality of ion optical elements. Each ion optical element of the first plurality has a recess structure adapted to receive a complimentary registration structure, a registration structure aligning an ion optical element of the first plurality with respect to at least one other ion optical element of the first plurality when the registration structure is registered in a complimentary recess structure when the compressive force is applied by the front securing member.

In various embodiments, the alignment of the ion optical elements by compressing them with the securing members, as described in the present teachings, can simplify the alignment and assembly of ion optical elements. In the present teachings, no torque pattern is required to compress and align the ion optical elements. In various embodiments, the securing members can lock the ion optics elements in place, so no additional parts are required to secure the ion optic assembly for shipping.

In various aspects, the present teachings provide systems for mounting and aligning ion optic components that facilitate their alignment. In various embodiments, provided are systems comprising a mounting base having a plurality of pairs of protrusions protruding from a mounting surface of the base and one or more mounting structures associated with each pair of protrusions. At least one electrical connection element is associated with each pair of protrusions, the connection elements passing through the mounting base from a back surface to the mounting surface. The systems further comprise two or more ion optic component supports, where each ion optic component support has a pair of recesses configured to receive one or more of the plurality of pairs of protrusions. The recess are configured such that when the pair of recesses of an ion optic component support is brought into registration with the corresponding pair of protrusions (by mounting an ion optic component to the mounting base using the one or more mounting structures associated with the pair of protrusions) an ion optics component mounted in the support is substantially aligned with another ion optics component so mounted and an electrical connection site on said ion optics component is proximate to a corresponding electrical connection element.

In various embodiments, the plurality of pairs of protrusions are configured such that only one orientation of an ion optic component support will enable the corresponding recesses in an ion optic component support to be brought into registration with the corresponding pair of protrusions. For example, in various embodiments, unique recess and protrusion patterns can be used to orient an ion optic component support. In various embodiments, the pairs of protrusions are configured to have different shapes for different ion optic components. In various embodiments, the systems for mounting and aligning ion optic components facilitating, for example, the rapid change out of optical components without fear of interchanging components or misorienting them.

Mass Analyzer Systems

In various aspects, the present teachings provide MALDI-TOF mass analyzer systems. In various embodiments, a mass analyzer system comprises (a) an optical system configured to irradiate a sample on a sample surface with a pulse of energy such that the pulse of energy strikes a sample on the sample surface at an angle substantially normal to the sample surface; (b) a MALDI ion source of the present teachings; (c) an ion deflector configured to deflect ions from a first ion optical axis along which ions are extracted into the mass analyzer system and onto a second ion optical axis; (d) a first substantially field free region positioned between the ion deflector and a timed ion selector, the timed ion selector being positioned between the first substantially field free region and a collision cell; (e) a second time-of-flight positioned between the collision cell and a first ion detector; (f) an ion mirror positioned between the second time-of-flight and the first ion detector; and (g) a second time-of-flight positioned between the ion mirror and a second ion detector. The timed ion selector is positioned to receive ions traveling along the second ion optical axis and is configured to select ions for transmittal to the collision cell.

In various embodiments, the MALDI ion source comprises a first electrode spaced a part from a sample support having a sample surface, a second electrode spaced apart from the first electrode in a direction opposite the sample support, and a third electrode spaced apart from the second electrode in a direction opposite the first electrode. The sample support, first, second and third electrodes are electrically coupled to a power source which is adapted to: (a) apply a first potential to the sample surface and a second potential to at least one of the first electrode and the second electrode to establish a non-extracting electric field at a first predetermined time substantially prior to striking a sample on the sample surface with a pulse of energy to form sample ions, the non-extracting electrical field substantially not accelerating sample ions in a direction away from the sample surface; (b) change the electrical potential of at least one of the sample surface and the first electrode to establish a first extraction electric field at a second predetermined time subsequent to the first predetermined time, the first extraction electric field accelerating sample ions in a first direction away from the sample surface; and (c) apply a third potential to the second electrode to focus ions in a direction substantially perpendicular to the first direction.

In various embodiments, the non-extracting electrical field can be a retardation electrical field which retards the motion of sample ions in a direction away from the sample surface. In various embodiments, the non-extracting electrical field can be a substantially zero electrical field, e.g., a substantially electrical field free region is established. A substantially zero electrical field can be established, e.g., when the first potential and the second potential are substantially equal.

In various embodiments, a mass analyzer system further comprises a vacuum lock chamber and a sample chamber connected to the vacuum lock chamber. A sample support changing mechanism is disposed in the vacuum lock chamber and a sample support transfer mechanism is disposed in the sample chamber. The sample support transfer mechanism configured to extract a sample support from a loading region of the sample support changing mechanism such that the sample support is registered within a frame in the sample support transfer mechanism. The sample support transfer mechanism is mounted on a multi-axis translation stage such that the sample support can be translated to a position where sample ions can be generated by laser irradiation of a sample on the surface of the sample support by a pulse of energy while said sample support is held in the sample support transfer mechanism, the sample support transfer mechanism is in the sample chamber, and said sample ions can be extracted along the first ion optical axis.

In various embodiments, a mass analyzer system further comprises one or more temperature controlled surfaces disposed therein.

In various embodiments, the timed ion selector and the collision cell comprise portions of an ion optical assembly, the ion optical assembly comprising a first plurality of ion optical elements disposed between a front member and a front side of a mounting body. The front member is attached to the mounting body by at least one attachment member and the front member has a threaded opening configured to accept a threaded surface of a front securing member. The mounting body contains the collision cell and the timed ion selector comprises at least one of the ion optical elements. The threaded opening of the front member is configured such that when the threaded surface of the front securing member is engaged in the threaded opening of the front member, a contact face of the front securing member can contact an ion optical element of the first plurality and apply a compressive force against the first plurality of ion optical elements. Each ion optical element of the first plurality has a recess structure adapted to receive a complimentary registration structure, a registration structure aligning an ion optical element of the first plurality with respect to at least one other ion optical element of the first plurality when the registration structure is registered in a complimentary recess structure when the compressive force is applied by the front securing member.

In various aspects, the present teachings provide methods for operating MALDI-TOF mass analyzer systems having two or more modes of operation and an ion source comprising a sample support having a sample surface, a first electrode spaced apart from the sample support, a second electrode spaced apart from the first electrode in a direction opposite the sample support holder, and a third electrode spaced apart from the second electrode in a direction opposite the first electrode. In various embodiments, the methods for a first mode of operation (a) select for the first mode of operation the position of a time-focus plane of the ion source in a direction z by application of an electrical potential difference between the sample surface and the first electrode, where this potential difference is established by applying a first electrical potential to the sample surface and a second electrical potential to the first electrode; and focusing ions in a direction substantially perpendicular to the direction z by application of a third electrical potential to the second electrode; (b) irradiate a sample on the sample surface with a pulse of energy at an irradiation angle that is substantially normal to the sample surface to form sample ions by matrix-assisted laser desorption/ionization; (c) extract sample ions in a direction substantially normal to the sample surface along a first ion optical axis which is substantially coaxial and substantially coincident with the pulse of energy; and (d) deflect sample ions from the first ion optical axis and onto a second ion optical axis for mass analysis using the first mode of operation. The mode of operation of the mass analyzer system is then changed to a second mode of operation; and the methods (a) select for the second mode of operation the position of a time-focus plane of the ion source in a direction z by application of an electrical potential difference between the sample surface and the first electrode, where this potential difference is established by applying a fourth electrical potential to the sample surface which is substantially equal to the first electrical potential, and applying a fifth electrical potential to the first electrode; and focusing ions in a direction substantially perpendicular to the direction z by application of a sixth electrical potential to the second electrode; (b) irradiate a sample on the sample surface with a pulse of energy at an irradiation angle that is substantially normal to the sample surface to form sample ions by matrix-assisted laser desorption/ionization; (c) extract sample ions in a direction substantially normal to the sample surface along a first ion optical axis which is substantially coaxial and substantially coincident with the pulse of energy; and (d) deflect sample ions from the first ion optical axis and onto a second ion optical axis for mass analysis using the second mode of operation.

In various embodiments where one of the modes of operation comprises collision induced dissociation, the methods for operating MALDI-TOF mass analyzer systems can include various embodiments of the present teachings of methods for focusing ions for a collision cell of the and can include various embodiments of the present teachings of methods for operating an ion optics assembly.

BRIEF DESCRIPTION OF THE DRAWINGS

The foregoing and other aspects, embodiments, objects, features and advantages of the invention can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the invention.

FIG. 4A depicting a sample support transfer mechanism portion and FIG. 4B a sample support changing mechanism portion.

DETAILED DESCRIPTION OF VARIOUS EMBODIMENTS

In various aspects, the present teachings provide novel MALDI-TOF systems. In various embodiments, provided are novel MALDI-TOF systems comprising one or more novel components such as, for example, sample support handling mechanisms, ion sources, ion optics and ion optical assemblies. In various embodiments, provided are novel methods for use with a mass spectrometry system to, for example, provide sample ions, focus sample ions, operate a mass spectrometry system in different operational modes, and operate ion fragmentors.

Figure 1A:
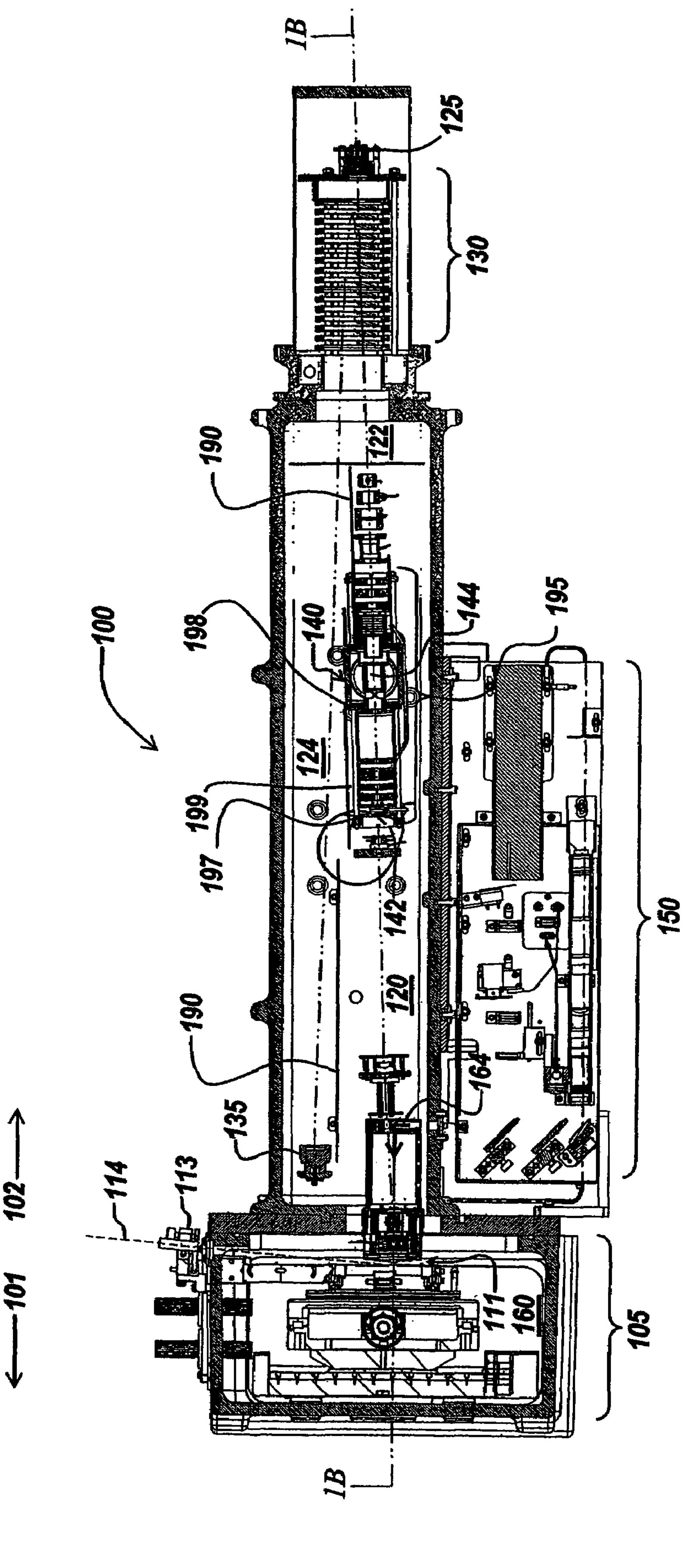
FIG. 1A depicts a front sectional view of various embodiments of a MALDI-TOF system of the present teachings.
Figure 1B:
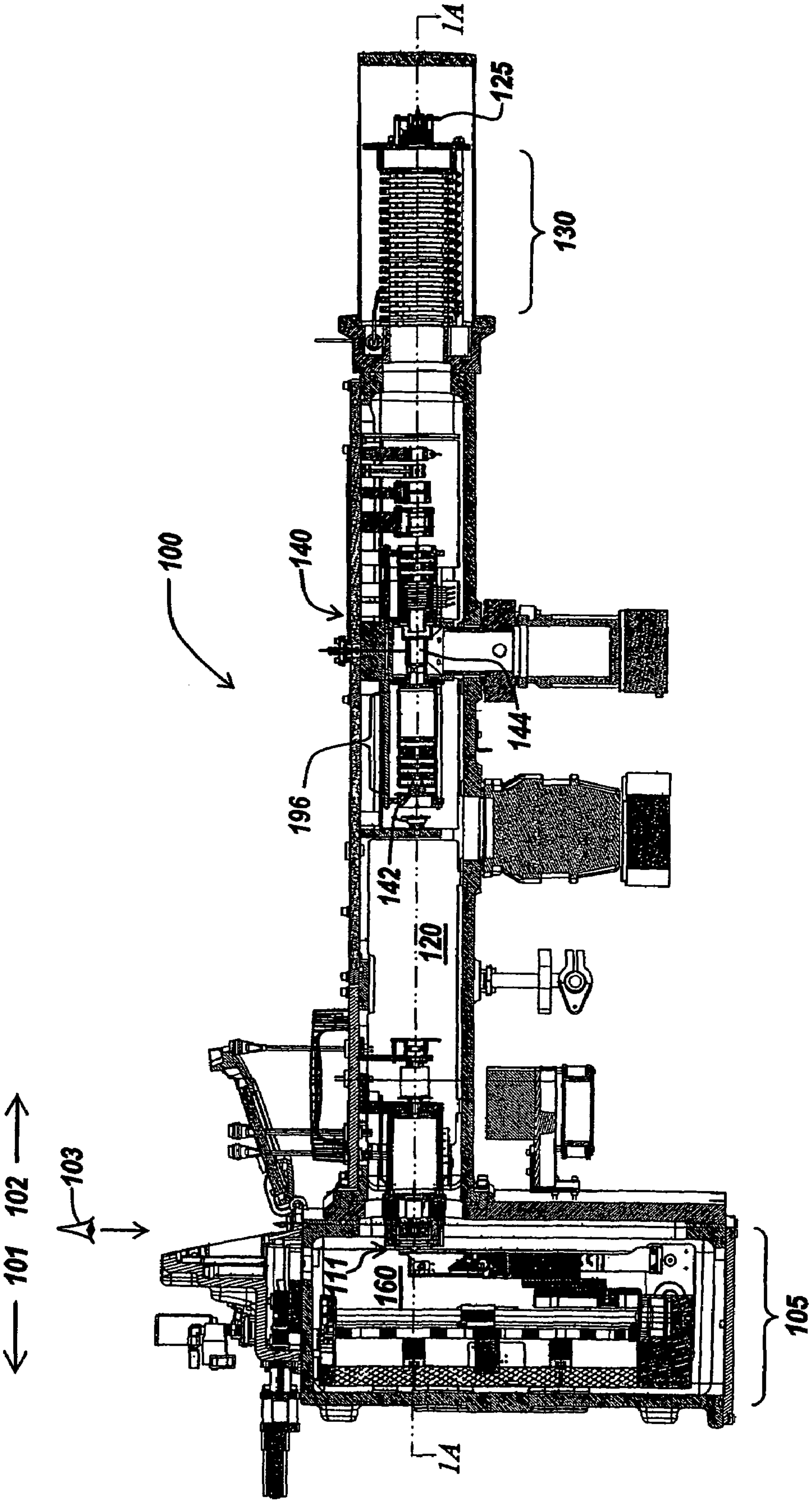
FIG. 1B depicts a side sectional view of various embodiments of a MALDI-TOF system of the present teachings.
Figure 1C:
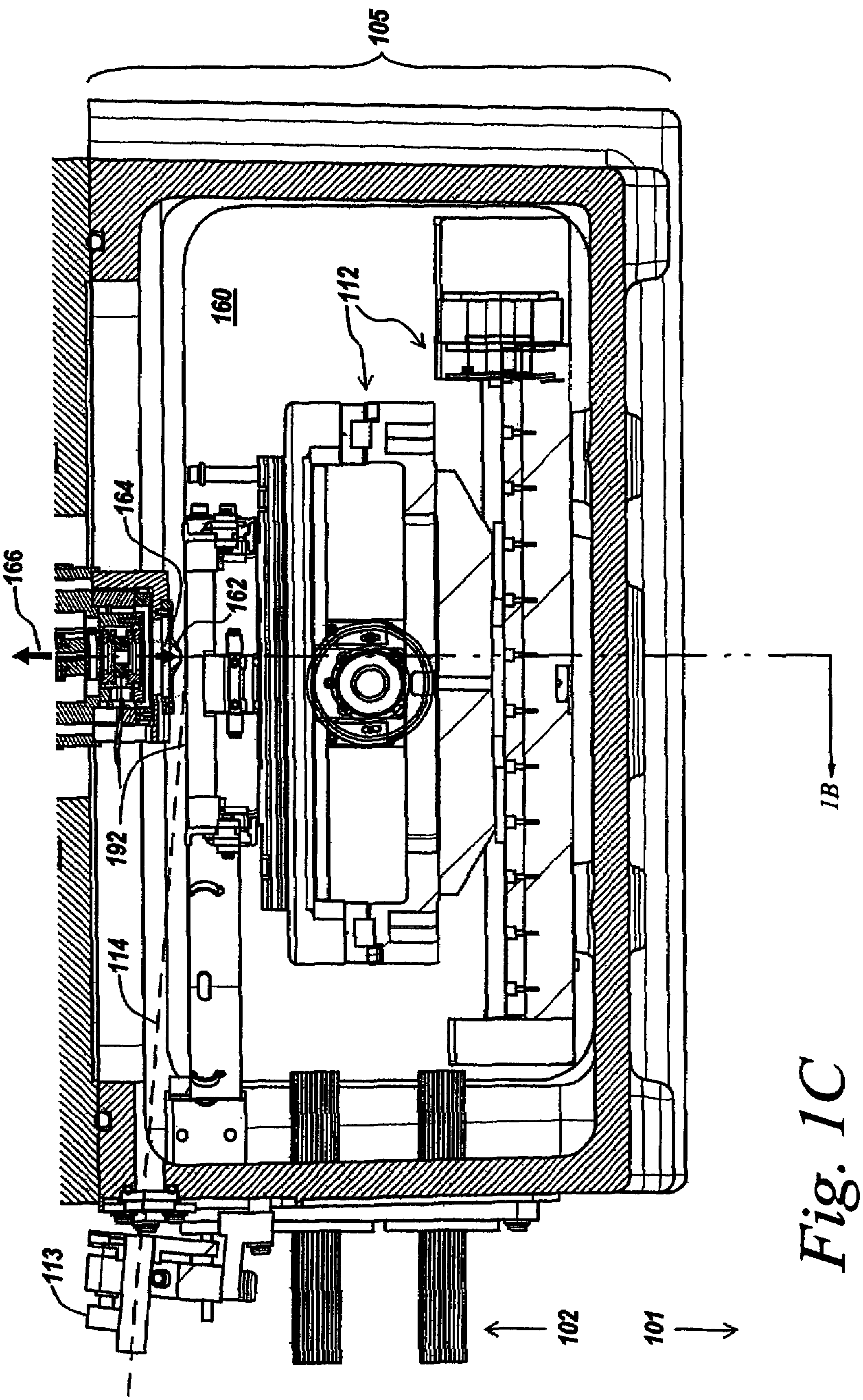
FIGS. 1C and 1D depict expanded portions, respectively, of FIGS. 1A and 1B, focused on the vacuum lock chamber, sample chamber and an ion formation region.
Figure 1D:
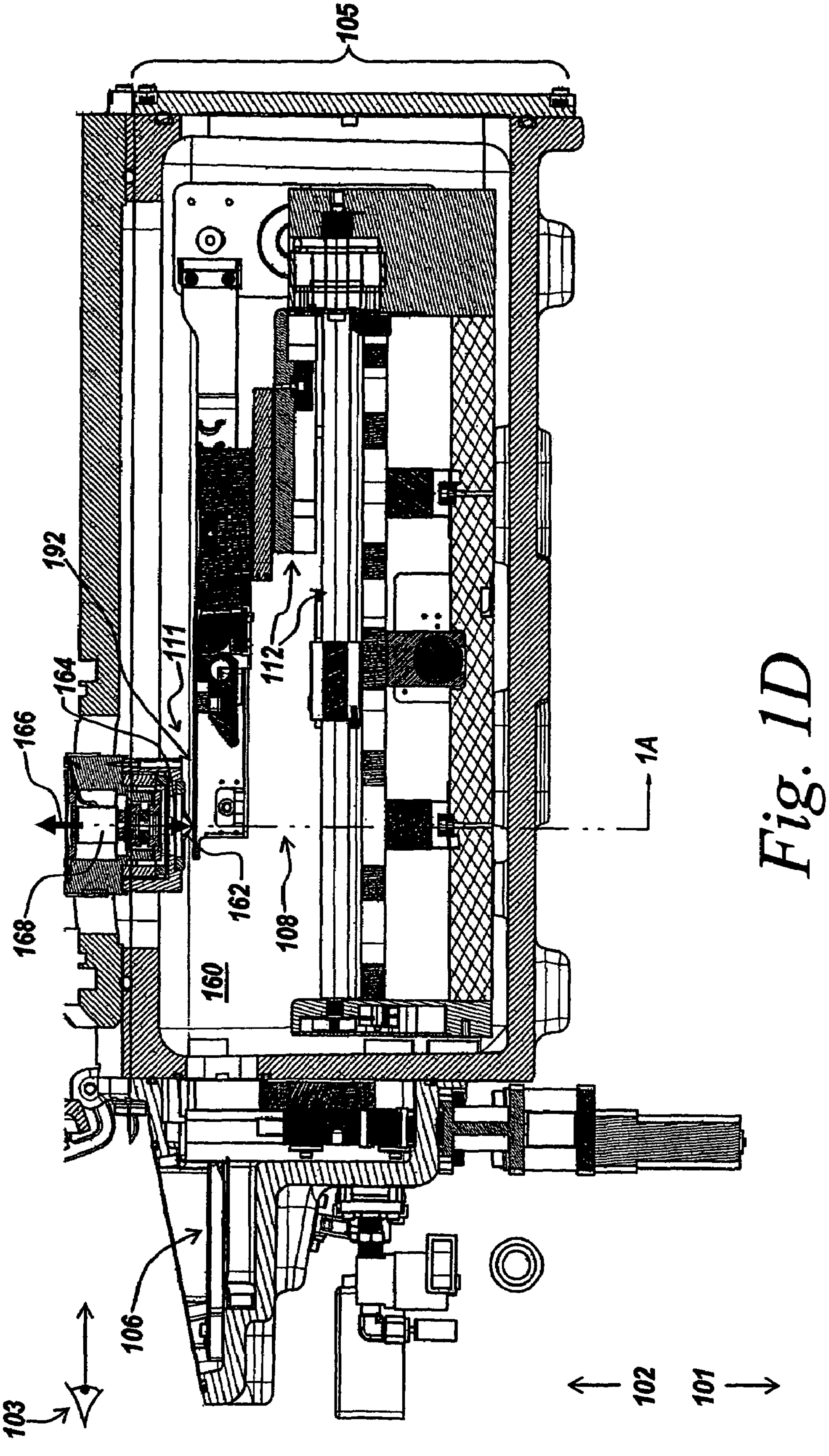

FIGS. 1A-1D depict substantially to scale views of a MALDI-TOF system 100 in accordance with various embodiments of the present teachings. FIG. 1A depicting a front sectional view, FIG. 1B a side sectional view, and FIGS. 1C and 1D presenting expanded views of portions of FIGS. 1A and 1B, respectively. To facilitate the viewing of FIGS. 1A-1D, the system 100 can be oriented such that the floor is in direction 101, the ceiling in direction 102, and the "front" of the instrument can be considered to be from viewpoint 103.

The various embodiments illustrated by FIGS. 1A-1D are not intended to be limiting. For example, a MALDI-TOF system in accordance with the present teachings can comprise fewer system components than illustrated or more system components than illustrated in FIGS. 1A-1D. In addition, the MALDI-TOF systems of the present teachings are not necessarily limited to the arrangement of the parts illustrated in FIGS. 1A-1D; rather, the illustrated arrangements are but some of the many modes of practicing the present teachings. For example, various embodiments of the systems illustrated in FIGS. 1A-1D can be operated in various modes, such as, e.g., linear MS operation, ion mirror MS operation, MS/MS operation, etc.

In various embodiments, a MALDI-TOF system 100 of the present teachings comprises a sample support handling system 105 comprising a vacuum lock chamber 106, through which sample supports can be loaded and removed, and a sample support transfer mechanism 108 configured to transport sample supports from the vacuum lock chamber 106 to an ion region 111. The sample support transfer mechanism can comprise a translation mechanism for translating the sample support in one or more dimensions within the ion source region to, for example, facilitate the serial analysis of two or more samples on the sample support. In various embodiments, the translation mechanism comprises an multi-axis (e.g., two dimension, x-y; three dimension x-y, -z) translational stage 112. The mass spectrometry system can comprise a viewing system 113 to view along a line of sight 114, e.g., the samples on the surface of a sample support when the sample support is positioned for ion formation in the ion source region.

The various embodiments of a MALDI-TOF system illustrated in FIGS. 1A-1D can be operated in various modes, e.g., linear MS operation, ion mirror MS operation, MS/MS operation, etc., and can comprise one or more regions substantially free of electrical fields 120, 122, 124. For example, in various embodiments, the TOF system can be operated as a linear TOF mass spectrometer. In linear TOF operational mode, ions produced in the ion source region 111 are extracted by electrical fields established by one or more ion source electrodes into a first region substantially free of electrical fields (a first field free region) 120 and travel to a first detector 125.

In various embodiments, the TOF system can be operated as a reflectron TOF mass spectrometer. In ion mirror TOF operational mode, after drifting through one more substantially electrical field free regions 120, 122, ions enter an ion mirror to, e.g., correct for differences in ion kinetic energy. The ions exiting the ion mirror 130 can then drift through another field free region 124 to a detector 135.

In various aspects, the MALDI-TOF system can serve and be operated as a MS/MS instrument. For example, in various embodiments, the MALDI TOF system comprises an ion fragmentor 140. Ions produced in the ion source region 111 are extracted by electrical fields established by one or more ion source electrodes into a first region substantially free of electrical fields (a first field free region) 120 and a timed ion selector 142 can be used to select ions for transmittal to, e.g., a collision cell 144, of the ion fragmentor, and fragment ions extracted into a second region substantially free of electrical fields (a second field free region) 122 to travel to a first detector 125, e.g., when performing linear-linear TOF, or travel to a second detector 135, e.g., when performing linear-reflector TOF.

In various aspects and embodiments, the present teachings utilize a pulse of energy to form sample ions. The pulse of energy can be coherent, incoherent, or a combination thereof. In various embodiments the pulse of energy is a pulse of laser energy. A pulse of laser energy can be provided by a laser system 150, for example, by a pulsed laser or continuous wave (cw) laser. The output of a cw laser can be modulated to produce pulses using, for example, acoustic optical modulators (AOM), crossed polarizers, rotating choppers, and shutters. Any type of laser of suitable irradiation wavelength for producing sample ions of interest by MALDI can be used with the present teachings, including, but not limited to, gas lasers (e.g., argon ion, helium-neon), dye lasers, chemical lasers, solid state lasers (e.g., ruby, neodinium based), excimer lasers, diode lasers, and combination thereof (e.g., pumped laser systems).

Sample Handling Mechanisms

Mass spectrometer systems can be complex instruments requiring accurate and repeatable alignment of components. One area where accurate and repeatable alignment is generally required is in the ion source. In MALDI-TOF mass analyzer systems, variations in the positioning of samples in the direction of ion extraction (referred herein as the Z direction) lead to variations in flight length (flight time), which can decrease mass resolution. In addition, variations in Z position, as well as X and Y position, can lead to formation of sample ions at positions where the ion optics of the instrument have not be tuned, which can decrease ion signal and resolution. These variations can be of even greater concern when investigations require the analysis of large numbers of samples necessitating repeated loading and unloading of samples, typically carried on sample supports such as, e.g., MALDI plates, from the ion source region of the mass analyzer system.

In various aspects, the present teachings provide sample support handling mechanisms. In various embodiments, the sample support handling mechanisms comprise a sample support changing mechanism and a sample support transfer mechanism, that can be configured to allow a user to place a sample support in the changing mechanism, which when captured by a sample support transfer mechanism for transfer to an ion source region, is registered in the X, Y and Z directions, facilitating the accurate and repeatable alignment of the samples in the X, Y and Z directions in the ion source. In various embodiments, the sample support handling mechanism is configured such that a sample support is registered to a position in the sample support transfer mechanism to: (a) within about ±0.002" in the Z direction; (b) within about ±0.005" in the X direction; (c) within about ±0.005" in the Y direction; (d) or combinations thereof. In various embodiments, the sample support handling mechanism is configured such that a sample support is registered to a position in the sample transfer mechanism to: (a) within about ±0.005" in the Z direction; (b) within about ±0.01" in the X direction; (c) within about ±0.01" in the Y direction; (d) or combinations thereof. In various embodiments, the sample support is capable of holding a plurality of samples.

In various embodiments, a sample support comprises a plate, e.g., a 3.4"×5" plate, a microtiter sized MALDI plate, etc. Suitable sample supports include, but are not limited to, 64 spot, 96 spot and 384 spot plates. An electrically insulating layer can be interposed between the sample and sample surface of the sample support. The sample can include a matrix material that absorbs at a wavelength of the pulse of laser energy and which facilitates the desorption and ionization of molecules of interest in the sample.

In addition to misalignment of sample support positions, distortions in the electrical field lines near a sample undergoing ionization can also lead to decreased ion signal and resolution. For example, discontinuities in electrical field lines close to samples undergoing MALDI can disturb the ion extraction electrical field lines, causing the path of the ion plume to deviate from the desired flight to an extraction electrode.

In various embodiments, the sample support handling mechanisms of the present teachings provide a frame having an electrically conductive surface and which substantially surrounds the sample support to extend the electrically conductive area around the sample support.

Figure 2:
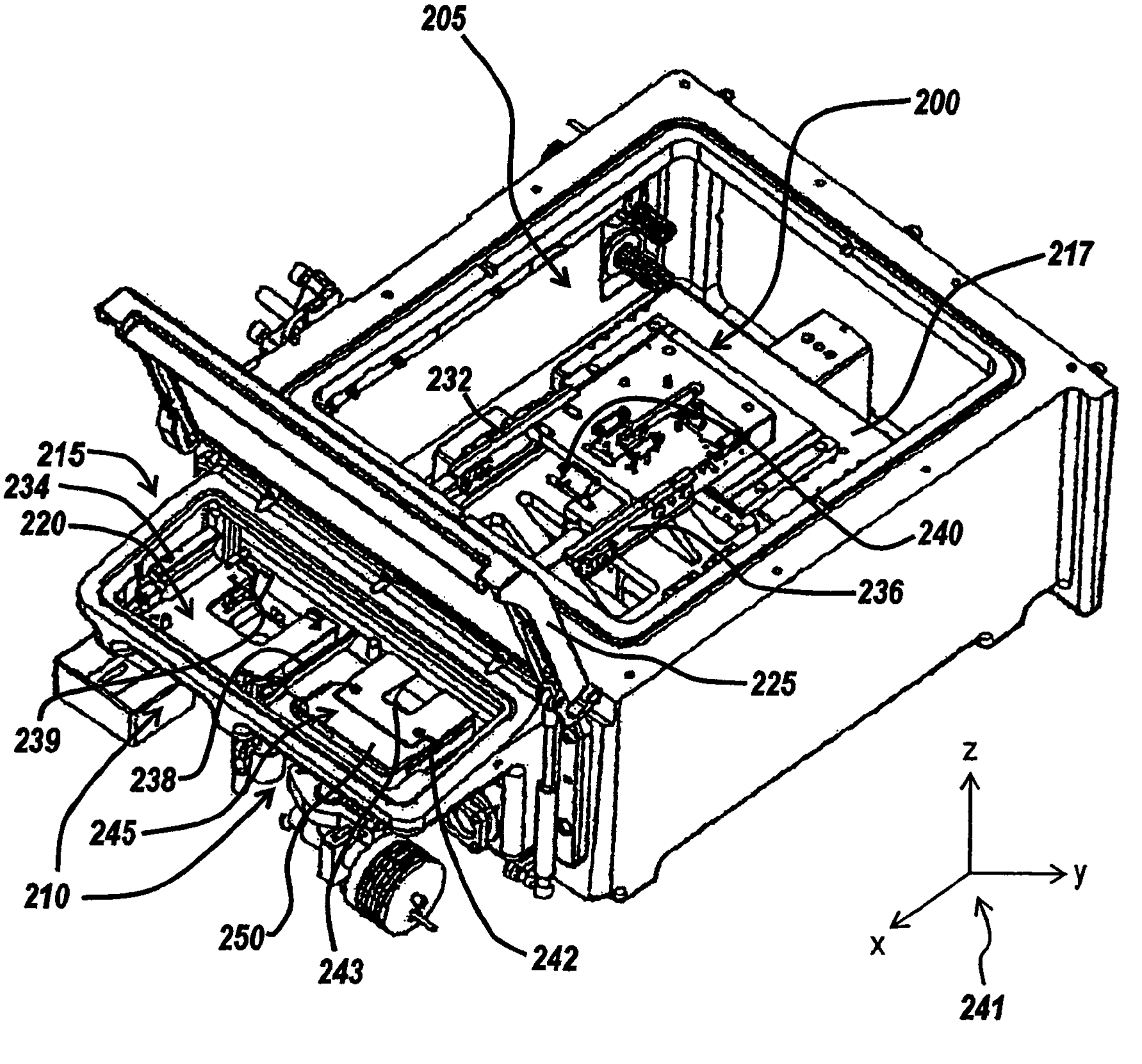
FIG. 2 depicts an isometric view of a sampling support handling mechanism and vacuum lock chamber in accordance with various embodiments of the present teachings.

Referring to FIG. 2, in various embodiments, a sample support handling mechanism of the present teachings comprises a sample support transfer mechanism 200 disposed in a sampling chamber 205 and a sample support changing mechanism 210 disposed in a vacuum lock chamber 215. In various embodiments, the sample support transfer mechanism 200 comprises a translation stage 217 (e.g. a two axis or three axis stage). The sample support transfer mechanism is disposed in the sample chamber but can extend a portion into the vacuum lock chamber to extract a sample support from and return a sample support to the sample support changing mechanism.

In operation, a sample support can be placed in a loading region 220 (e.g., onto a load pad) of the changing mechanism 210 in the vacuum lock chamber 215, and the vacuum lock chamber door 225 closed. The vacuum lock chamber is pumped down (e.g., to about 80 mTorr or lower) and a sample chamber door (e.g., a gate valve) between the vacuum lock and sample chambers opened. The sample support transfer mechanism can be translated in a Y direction until a left arm 232 is sufficiently aligned with a left cam structure 234 of the changing mechanism and a right arm 236 is sufficiently aligned with a central cam structure 238 of the changing mechanism. The sample transfer mechanism can be then translated in the X direction so the left and right arms 232, 236 can engage and capture the sample support (not shown in FIG. 2 for the sake of clarity in illustrating other structures) in the loading region 220. As the left and right arms approach the sample support, the left cam structure 234 and central cam structure 238 engaging, respectively, left and right bearing support structures of, respectively, the left and right arms, urging them to a second position (e.g., pushing them down) and a first disengagement member 239 urges an engagement member 240 to a second position (e.g., pushing it down) allowing a sample support to be engaged against a front face of the transfer mechanism. In various embodiments, a frame for the sample support (not shown in FIG. 2 for the sake of clarity in illustrating other structures) can be between the left and right arms prior to engagement of a sample support in the loading region, or on the sample support in the loading region. When, e.g., the frame is between the left and right arms (see, e.g., FIG. 3) the transfer mechanism is aligned in such a manner that the frame is slightly above the sample support to allow the frame to pass over the sample support without substantially contacting samples of interest thereon. In various embodiments, the sample support (not shown in FIG. 2 for the sake of clarity in illustrating other structures) can be in a frame when it is loaded into the loading region, the sample transfer mechanism engaging and loading the framed sample support. When, e.g., the sample support is in a frame prior to engagement by the sample transfer mechanism, the frame can be registered within the transfer mechanism. After capture of the sample support, the sample support can be translated into the sample chamber, the sample chamber door closed, the sample chamber pumped down to a pressure suitable for ion formation, and the formation of ions begun by, e.g., MALDI. In the illustrated sample chamber of FIG. 2, sample ions are extracted from the sample chamber substantially in the direction Z. The X, Y and Z directions in the isometric view of FIG. 2 being schematically illustrated by the inset coordinates 241.

In operation, to remove a sample support, e.g., after MALDI analysis, the sample transfer stage can be translated in the Y direction until the left arm 232 is sufficiently aligned with a central cam structure 234 of the changing mechanism and the right arm 236 is sufficiently aligned with a right cam structure 242 of the changing mechanism. The sample transfer mechanism can be then translated in the X direction so the left and right arms 232, 236 can engage, respectively, the central 238 and right cam structures 242 and a second disengagement member 243 can disengage the engagement member 240 on the transfer mechanism. In various embodiments, the engagement member comprises rollers that can follow the surface (e.g., the under surface of the disengagement member 243) of a sloped second disengagement member 243, thereby allowing a sample support to slowly disengage (e.g., without abruptly dropping) into the unloading region 245 and depressing a sample support capture member 250. As the sample transfer mechanism continues to travel in the X direction the sample support becomes fully disengaged from the left and right arms of the transfer mechanism, the leading edge (the edge furthest into the unloading region) of the sample support (and/or frame member in which it may be retained) places pressure against the capture member, and the engagement member 240 becomes fully disengaged from the sample support. In various embodiments, when the leading edge of the sample support (and/or frame member in which it may be retained) clears the outer edge of the capture member 250, the capture member engages (e.g., springs up) the sample support (and/or frame member in which it may be retained) preventing the sample support from being withdrawn with the transfer mechanism.

Figure 3:
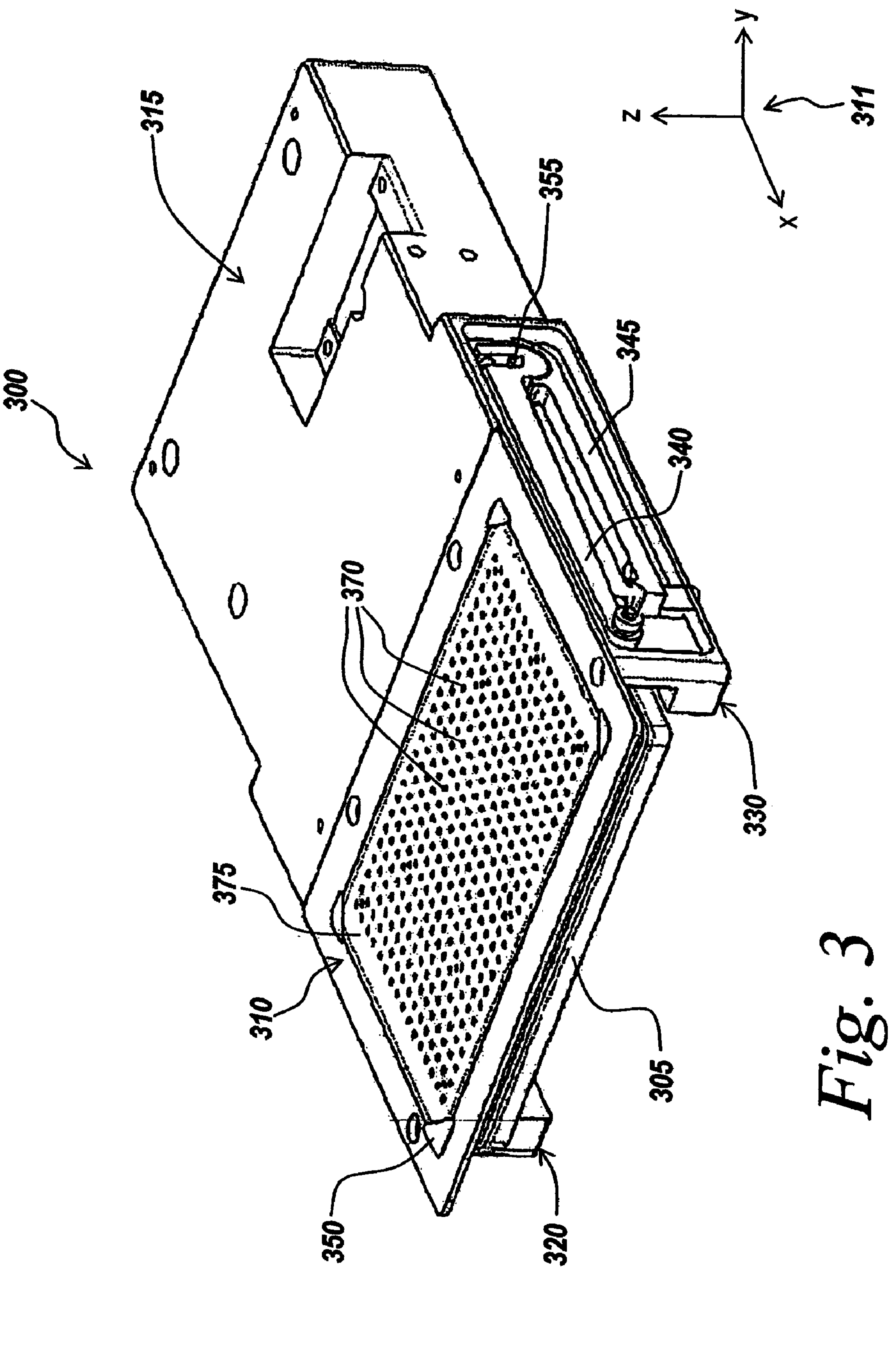
FIG. 3 depicts an isometric view of a sample support transfer mechanism with loaded sample support of a sampling support handling mechanism in accordance with various embodiments of the present teachings.

FIG. 3 depicts an expanded portion of a sample support transfer mechanism 300, in accordance with various embodiments of a sample handling mechanism of the present teachings, showing a captured sample support 305 and a frame 310. The X, Y and Z directions in the isometric view of FIG. 3 being schematically illustrated by the inset coordinates 311. Referring to FIG. 3, the sample support transfer mechanism comprises a base 315, a left arm 320 and a right arm 330 which are substantially perpendicular to a front face (obscured by the sample support 305 and frame 310 in this illustration). In various embodiments, the base 315 of the transfer mechanism attaches to an X-Y translation stage within the sample chamber. The translation stage can be used to move samples to an ion formation region as well as transferring the sample support between the vacuum lock and sample chambers.

In various embodiments, the right arm bearing support structure comprises a pivot arm 340 and a clamp arm 345. During translation into a loading region or unloading region of the changing mechanism, the central cam structure (loading operation) or right cam structure (unloading operation) of the changing mechanism engage the pivot arm 340 urging from a first position and down into a second position (loading operation) or third position (unloading operation), which in turn pushes down the clamp mechanism 345 allowing the right arm to engage a sample support (loading operation) or disengage a sample support (unloading operation).

For example, in various embodiments, in a loading operation as the transfer stage is driven in the X direction into the loading region, the left arm 330 of the sample support handling mechanism actuates the registration member (a rocker arm in FIG. 4B) of the loading region. The registration member pushes the sample support into the corner of the sample support transfer mechanism where the left arm meets the front face of the base 315. As the transfer mechanism continues in the X direction into the loading region, the pivot 340 arm is released, and the clamp arm 345 pushes the sample support against the retaining structures 350 on the frame, registering the back side (i.e., the side of the sample support farther from the front face of the base) of the sample support plate in the Z direction.

In various embodiments, the frame comprises an electrically conductive surface on at least the surface which faces the ion extraction electrode(s) of the ion source. In various embodiments, extending the electrically conductive area around the sample support facilitates reducing electrical field line discontinuity between the sample support and extraction electrode(s). In various embodiments, the corners of the frame up against which a sample support can be registered in the Z direction, have a low profile to facilitate reducing electrical field disturbance.

In various embodiments, the pivot arm and clamp arm are substantially duplicated on both the right arm 330 and the left arm 320 of the transfer mechanism, e.g., for actuation from either side. Motion can be transferred from an active side to a slave side by, e.g., a solid rod 355 at the pivot point. In an unloading operation, for example, the transfer mechanism can be driven in the X direction into the unloading region, one or more of the cam structures engaging one or more of the bearing support structures to disengage the clamping arms, and a second disengagement member disengages the engagement member, allowing the sample support to drop out from between the left and right arms of the transfer mechanism. As the transfer mechanism retracts from the unloading region, a capture mechanism (illustrated as a stripper plate in FIG. 4B) prevents the sample support from following the sample support transfer mechanism as it retracts.

Figure 4A:
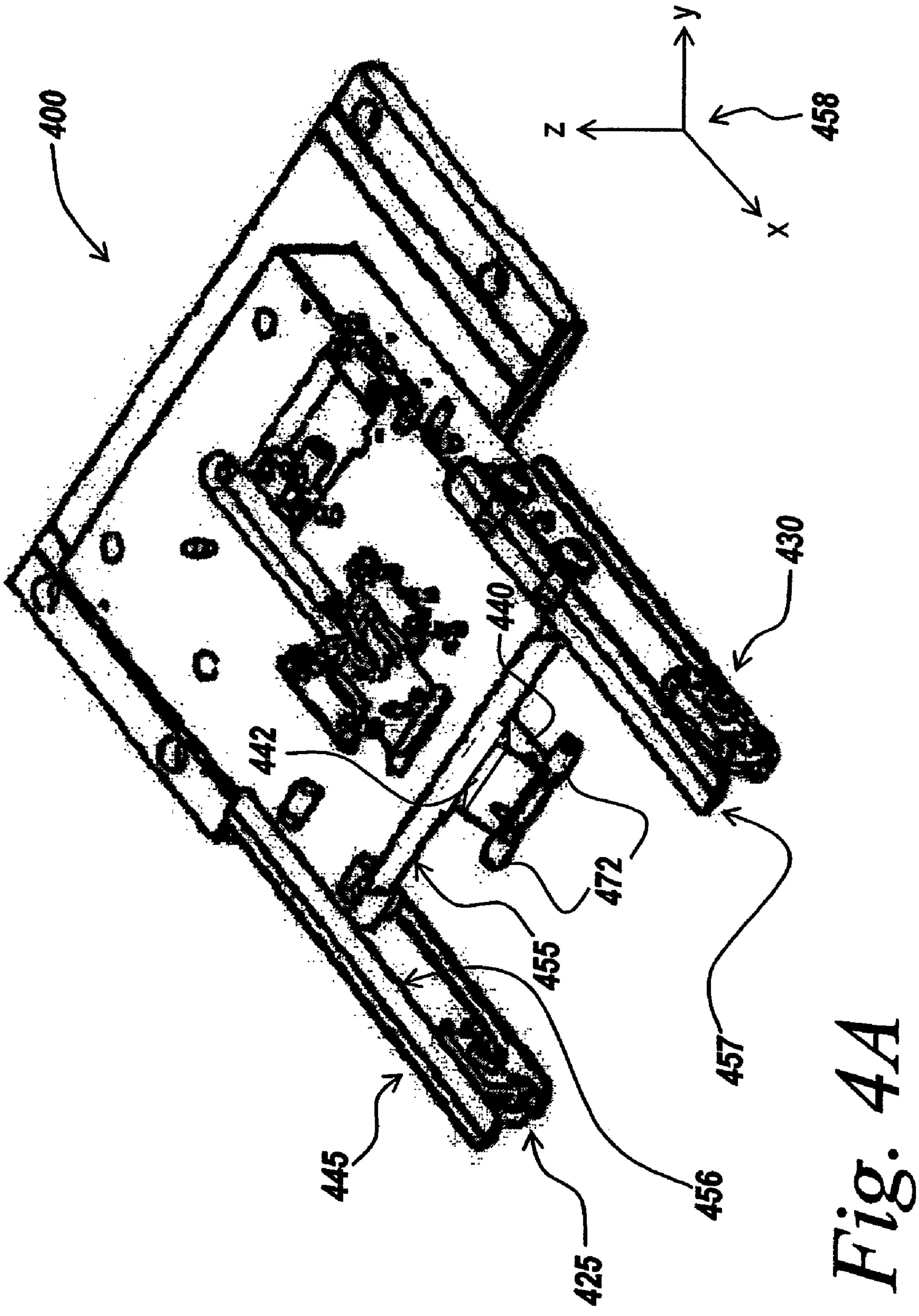
FIGS. 4A and 4B depict isometric views of a sampling support handling mechanism in accordance with various embodiments of the present teachings.
Figure 4B:
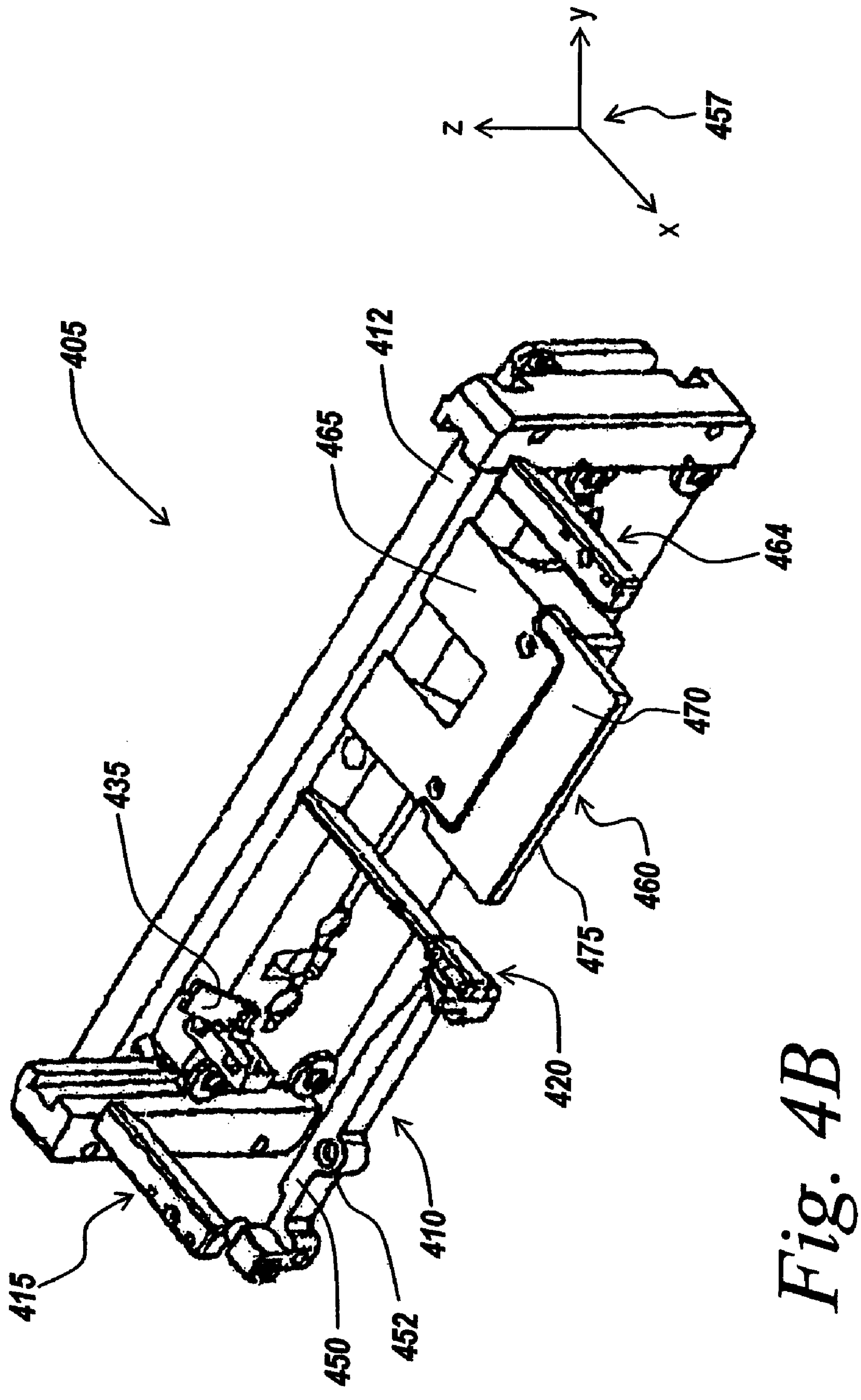

Referring to FIGS. 4A and 4B, expanded views of a sample support transfer mechanism portion (FIG. 4A) and a sample support changing mechanism portion (FIG. 4B), in accordance with various embodiments of a sample handling mechanism of the present teachings, are shown. The sample support handling mechanism comprises a sample support transfer mechanism 400 and a sample support changing mechanism 405, the sample changing mechanism being disposed in a vacuum lock chamber. Sample supports can be input and output through the vacuum lock chamber.

For example, in operation, a sample support can be placed in a loading region 410 of the changing mechanism 405 and the vacuum lock chamber door closed. The vacuum lock chamber is pumped down and when a desired vacuum is reached in the vacuum lock chamber, a door 412 separating the two chambers (e.g., a gate valve) can be opened.

Once the sample transfer mechanism is aligned in the Y direction with the loading region 410 it can be translated into the loading region 410 in the X direction. As the left and right arms approach the sample support, a left cam structure 415 and central cam structure 420 engaging, respectively, the left 425 and right 430 bearing support structures urging them to a second position (e.g., pushing them down) and a first disengagement member 435 urges the engagement member 440 to a second position (e.g., pushing it down). In various embodiments, the engagement member comprises an angled surface 442 sloped away from the front face 455 of the base member to facilitate, e.g., smooth registration of a sample support. In various embodiments, the front face 455 of the base member comprises bearings to facilitate, e.g., smooth registration of a sample support. As the transfer mechanism continues into the loading region, the left arm 445 engages the registration member 450 (illustrated as a rocker arm), e.g., on the left cam side of the rocker arm pivot 452, pivoting the rocker arm which in turn pushes the sample support against the front face 455 and left arm 445, and, in various embodiments, registers the sample support in the X-Y direction up against the left arm 445 and the front face 455 of the base. As the transfer mechanism continues into the loading region in the X direction, the engagement member reaches 440 reaches the end of the disengagement member 435, and the engagement member returns to its first position (e.g., springs up) registering the front side of the sample support (i.e., the side of the sample support nearer the front face of the base) in the Z direction and securing it in the X direction. In various embodiments, the sample support is registered in the Z direction against a retention projection (e.g., ledge) of the left arm 456 a retention projection (e.g., ledge) of the right arm 457. The retention projections extending in the Y direction only a portion of the distance between the two arms. As the transfer mechanism retracts from the loading region back into the sample chamber, the bearings support blocks spring back up (return to their respective first positions) and register the back side of the plate in the Z direction. The X, Y and Z directions in the isometric views of FIGS. 4A and 4B being schematically illustrated by the inset coordinates 458.

In operation, unloading of a sample support can proceed, for example, as follows. When a desired vacuum is reached in the vacuum lock chamber the door separating 412 the two chambers (e.g., a gate valve) can be opened. Once the sample transfer mechanism is aligned in the Y direction with the unloading region 460 it can be translated into the unloading region 460 in the X direction. As the left and right arms of the transfer mechanism approach they enter the unloading region, the central cam structure 420 and a right cam structure 464 engage, respectively, the left 425 and right 430 bearing support structures urging them to a third position (e.g., pushing them down) and a second disengagement 465 member urges the engagement member 440 to a third position (e.g., letting it disengage). In various embodiments, a ramp 465 slowly drops the engagement member 440 and the sample support engages a sample support capture mechanism 470 (e.g., illustrated as a spring loaded stripper plate in FIG. 4A) urging it from a first position to a second position (e.g., pushing it down). In various embodiments, the engagement member 440 comprises roller 472 which engage the second disengagement member 465. As the leading edge of the sample support passes over the outer edge 475 of the stripper plate 470, the stripper plate springs back up (e.g., to a third position) which retains the sample support in the unloading region as the transfer mechanism retracts back into the sample chamber.

In various aspects, the present teachings provide methods for providing sample ions for mass analysis. Referring to FIGS. 1A-4B, in various embodiments, the methods comprise supporting a plurality of samples 370 on a sample surface 375 of a sample support 305; providing a vacuum lock chamber 106, 215 having a region for loading a sample support 220 and a region for unloading a sample support 245; and providing a sample chamber 160, 205 having a sample transfer mechanism 108, 200 disposed therein The methods extract a sample support disposed in the region for loading 220 with the sample transfer mechanism 108, 200 such that the sample support is registered within a frame 310 in the sample support transfer mechanism, e.g., to within about ±0.002" in a Z direction, to within about ±0.005" in a X direction, and to within about ±0.005" in a Y direction, wherein the X, Y and Z directions are mutually orthogonal and the direction Z is substantially perpendicular to the surface of the sample support. The sample support is translated to a first position (e.g., to align a first sample on the sample surface with an ion source extraction electrode 162) within the sample chamber 160, 205 where a first sample on the surface of the sample support is irradiated with a with a pulse of energy 164 to form a first group of sample ions while the sample support is being held by the sample transfer mechanism and at least a portion of the first group of sample ions is extracted in the Z direction 166. The sample support is then translated to a second position (e.g., to align a second sample on the sample surface with an ion source extraction electrode 162) within the sample chamber where a second sample on the surface of the sample support is irradiated with a with a pulse of energy 164 to form a second group of sample ions while the sample support is being held by the sample transfer mechanism and at least a portion of the second group of sample ions is extracted in the Z direction 166. Further samples can be analyzed on the sample support prior to the sample support being placed by the sample support transfer mechanism in the region for unloading 245 a sample support. The methods continue with repeating the steps of extracting at least one other sample support followed by the steps of translating, irradiating and extracting for at least two samples on the sample support.

In various embodiments, at least one of the steps of irradiating a sample with a pulse of energy comprises irradiating the sample at an irradiation angle that is within 5 degrees or less of the normal of the surface of the sample support to form sample ions by matrix-assisted laser desorption/ionization. In various embodiments, at least one of steps irradiating a sample with a pulse of energy comprises irradiating the sample at an irradiation angle that is within 1 degree or less of the normal of the surface of the sample support to form sample ions by matrix-assisted laser desorption/ionization. In various embodiments, at least one of the steps of extracting at least a portion of the sample ions comprises extracting sample ions in the Z direction along a first ion optical axis, wherein the first ion optical axis is substantially coaxial with the pulse of energy.

For example, referring to FIGS. 1A-1D, in various embodiments, sample ions are extracted along a first ion optical axis 168 which is substantially coaxial and substantially coincident with the pulse of energy 164.

Ion Sources

In various aspects, the present teachings relate to MALDI ion sources and methods of MALDI ion source operation, for use with mass analyzers. In various aspects, the present teachings provide three-stage ion sources that, in various embodiments, facilitate compensating for the spread in ion arrival times due to initial ion velocity without substantially degrading the radial spatial focusing of the ions and while allowing for an adjustable velocity space focus plane. As is generally understood by those of ordinary skill in the art, the desired position of the velocity space focus plane is primarily determined by the mode of operation of a TOF instrument.

Figure 5:
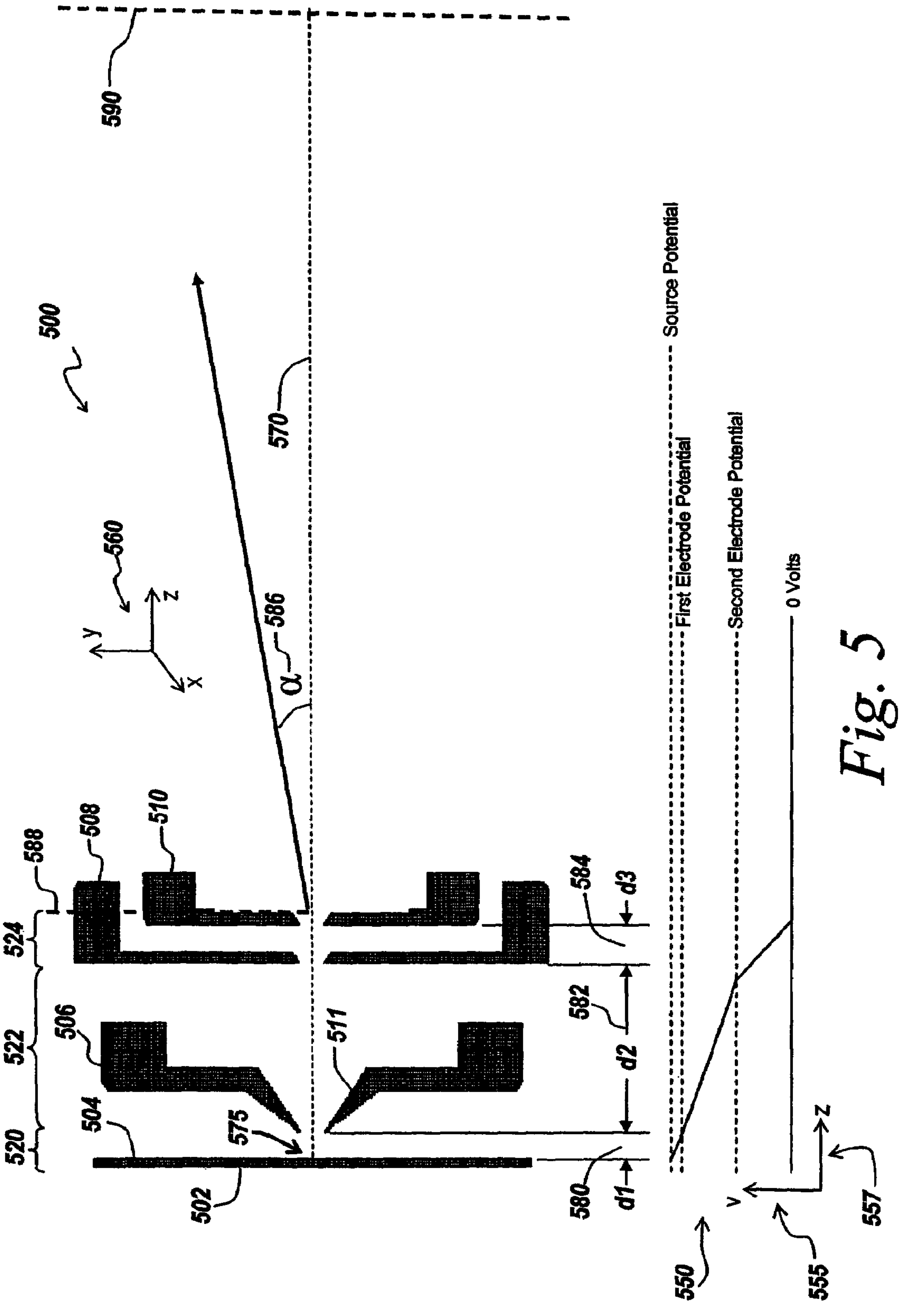
FIG. 5 schematically illustrates various embodiments of a three-stage ion source of the present teachings with illustrative ion trajectories.

Referring to FIG. 5, a three-stage ion source 500 of the present teachings comprises a sample support 502 having a sample surface 504, a first electrode 506, a second electrode 508, and a third electrode 510. In various embodiments, the first-stage 520 being defined by the sample surface 504 and first electrode 506, the second-stage 522 being defined by the first electrode 506 and the second electrode 508, and the third-stage 524 defined by the second electrode 508 and the third electrode 510. In various embodiments, the first-stage 520 being defined by the sample surface 504 and second electrode 508, the second-stage 522 being defined by the first electrode 506 and the second electrode 508, and the third-stage 524 defined by the second electrode 508 and the third electrode 510. A variety of electrode shapes and configurations can be used including, but not limited to, plates, grids, cones, and combinations thereof. For example, the first electrode 506 can be in the form of a skimmer, having a conical portion 511.

In various embodiments, the methods for operating of a TOF mass analyzer having two or more modes of operation comprise establishing an ion energy by setting an electrical potential difference between the sample surface 504 and the third electrode 510, and focusing ions by variation of the electrical potentials on one the first electrode 506 and the second electrode 508. In various embodiments, in a first mode of operation the position of a time-focus plane in a direction z is selected by applying a first electrical potential to the sample surface 504 and a second electrical potential to the first electrode 506 and ions are focused in a direction substantially perpendicular to the direction z by applying a third electrical potential to the second electrode 508. The refocusing of the TOF mass analyzer comprises the position of a time-focus plane in a direction z for the second mode of operation is selected by changing the electrical potential applied to the first electrode 506; and ions are focused in a direction substantially perpendicular to the direction z by changing the electrical potential applied to the second electrode 508.

Sample ions can be generated by irradiating a sample disposed on a sample surface of the holder with a pulse of energy. In various embodiments, to provide a velocity space focus plane and x, y spatial focusing, the three-stage ion source comprises a power source, electrically coupled to the sample support, first, second and third electrodes, which is adapted to: (a) apply a first potential to the sample surface and a second potential to at least one of the first electrode and the second electrode to establish a non-extracting electric field at a first predetermined time substantially prior to striking a sample on the sample surface with a pulse of energy to form sample ions, the non-extracting electrical field substantially not accelerating sample ions in a direction away from the sample surface; (b) change the electrical potential of at least one of the sample surface, the first electrode and the second electrode to establish a first extraction electric field at a second predetermined time subsequent to the first predetermined time, the first extraction electric field accelerating sample ions in a first direction away from the sample surface; and (c) apply a third potential to the second electrode to focus ions in a direction substantially perpendicular to the first direction. An electrical potential applied to one or more of the sample surface, first electrode, and second electrode to establish a non-extracting electrical field can be a zero potential. An electrical potential applied to one or more of the sample surface, first electrode, second electrode, and third electrode to establish one or more of the first extraction electrical field and to focus ions in a direction substantially perpendicular to the first direction, can be a zero potential.

In various embodiments, the non-extracting electrical field can be a retardation electrical field, the retardation electrical field retarding the motion of sample ions in a direction away from the sample surface. In various embodiments, the non-extracting electrical field can be a substantially zero electrical field, e.g., a substantially electrical field free region is established. A substantially zero electrical field can be established, e.g., when the first potential and the second potential are substantially equal.

Referring to FIG. 5, an example of the relative electrical potentials on the sample surface, first electrode, second electrode, and third electrode at the second predetermined time are illustrated in the inset schematic plot 550 of electrical potential 555 as a function of the z coordinate 557. The coordinate system for FIG. 1 and the data of Table 1 is shown by the inset coordinate system reference 560 where the z axis lies along the ion extraction axis 570, the y axis is perpendicular to the z axis in the plane of the figure and the x axis is perpendicular to the z axis out of the plane of the figure, and the origin is at the intersection 575 of the ion extraction axis 570 with the sample surface 504.

In some embodiments, both the first and second electrodes have apertures. In various embodiments, sample ions are extracted along a first ion optical axis 570 defined by the axis running through the centers of apertures in the first electrode 506 and the second electrode 508. In various embodiments, an optical system is configured to substantially align the pulse of laser energy with the first ion optical axis. For example, in various embodiments, sample ions are extracted along a first ion optical axis in a direction substantially normal to the sample surface and the pulse of energy is substantially coincident with the first ion optical axis. The third electrode can be an apertured electrode that is a substantially planar plate or grid. In various embodiments, the third electrode is positioned so the centers of the apertures of the first, second, third apertured electrodes substantially fall on a common axis.

Where the apertures in the first and second electrodes are substantially centered on the sample being irradiated and the first and second electrodes are substantially symmetric about the normal to the sample surface, the first ion optical axis will intersect the sample surface at an angle substantially normal to the sample surface, the extraction direction will be substantially normal to the sample surface, the extraction direction will be substantially parallel to the first ion optical axis, and sample ions will be extracted along the first ion optical axis.

The three-stage ion source of the present teachings can introduce an additional adjustable parameter for the ion source which can be used to compensate for changes to the x,y spatial focus characteristics of the ion beam due to optimizing the velocity space focus plane at particular position (in z). This additional parameter can allow the operator of a three-stage ion source of the present teachings to change the effective length of the second-stage of the ion source electrostatically; thus facilitating the optimization of the x,y space focus characteristics of the ion beam without compromising the position of the velocity space focus plane, which position is primarily dictated by the voltage ratio and geometry of the first-stage of the ion source. The behavior of a two-stage ion source and its operation to form a velocity space focus plane has been previously described, see for example, M. Vestal and P. Juhasz, J. American Soc. Mass Spec., 9, 892-911 (1998), the entire contents of which are hereby incorporated by reference.

Tables 1-6 compare ion beam characteristics for a three-stage ion source substantially as illustrated in FIG. 1 with a two-stage ion source (i.e., the source configuration of FIG. 1 operated without a potential on the third electrode). The data of Tables 1-6 was calculated using SIMION (v7.0, Idaho National Engineering and Environmental Laboratory) with the input parameters: d1 580 equaled 2 mm, d2 582 equaled 13.675 mm and, d3 584 equaled 3.175 mm, initial ion velocity equaled 300 m/s. Tables 1-6 compare ion beam divergence a (i.e., the angular deviation of the ion beam $\alpha$ at the source exit 586) (column 5) and the ion beam radial position (e.g., x or y) at two z positions, the source exit 588 (column 3) and at 74.4 mm 590 (column 4), for ions formed with various initial velocity vectors angles (column 1) with respect to the normal to the surface of the sample support. Column 2 lists the potential applied to the third electrode, the zero potential data corresponding in this case to two-stage operation of the ion source.

Tables 1-3 compare results for ions formed at the origin 575 with initial velocity vectors at 0, 15, 30 and 45 degrees with respect to the normal to the surface of the sample support. Tables 4-6 compare results for ions formed at +50 microns in the y direction initial velocity vectors at 0, 15, 30 and 45 degrees with respect to the normal to the surface of the sample support.

Tables 1-6 also compare ion beam characteristics for three operation modes, linear TOF, ion mirror TOF, and MS/MS TOF where the ion source was operated to provide a velocity space focus plane. Tables 1 and 4 present results for linear TOF mode operation with a 20 kV potential on the sample support and a 19.1 kV potential on the first electrode, and where the time delay for delayed extraction was 370 ns. Tables 2 and 5 present results for ion mirror TOF mode operation with a 20 kV potential on the sample support and a 16 kV potential on the first electrode, and where the time delay for delayed extraction was 600 ns. Tables 3 and 6 present results for MS/MS TOF mode operation with a 8 kV potential on the sample support and a 7.3 kV potential on the first electrode, and where the time delay for delayed extraction was 460 ns.

It is to be understood that although electrical potentials are given in Tables 1-6, that the absolute values of the potentials are not critical to the present teachings. Further, it is to be understood that although various electrical potentials are noted as zero or ground, this is purely for convenience of notation and conciseness in the equations appearing herein. One of skill in the art will readily recognize that it is not necessary to the present teachings that the potential at an electrode be at a true earth ground electrical potential. For example, the potential at the electrode can be a "floating ground" with an electrical potential significantly above (or below) true earth ground (e.g., by thousands of volts or more). Accordingly, the description of an electrical potential as zero or as ground herein should not be construed to limit the value of an electrical potential with respect to earth ground in any way.

TABLE 1

Linear TOF, On Axis

| Initial Ion Trajectory Angle (degrees) | Third Electrode Potential (V) | Ion Beam Radial Position (mm) Source Exit | Ion Beam Radial Position (mm) z = 74.4 mm | Spread Angle α (degrees) |
|---|---|---|---|---|
| 2 Stage | | | | |
| 0 | 0 | 0 | 0 | 0 |
| 15 | 0 | 0.0503 | 0.0123 | −0.029 |
| 30 | 0 | 0.0896 | 0.0257 | −0.049 |
| 45 | 0 | 0.1065 | 0.0297 | −0.059 |
| 3 Stage | | | | |
| 0 | 4400 | 0 | 0 | 0 |
| 15 | 4400 | 0.0679 | 0.0645 | $-2.62 \times 10^{-3}$ |
| 30 | 4400 | 0.1081 | 0.1132 | $3.93 \times 10^{-3}$ |
| 45 | 4400 | 0.1266 | 0.1307 | $3.16 \times 10^{-3}$ |

TABLE 2

Ion Mirror TOF, On Axis

| Initial Ion Trajectory Angle (degrees) | Third Electrode Potential (V) | Ion Beam Radial Position (mm) Source Exit | Ion Beam Radial Position (mm) z = 74.4 mm | Spread Angle α (degrees) |
|---|---|---|---|---|
| 2 Stage | | | | |
| 0 | 0 | 0 | 0 | 0 |
| 15 | 0 | 0.1421 | 0.4476 | 0.235 |
| 30 | 0 | 0.2411 | 0.7707 | 0.408 |
| 45 | 0 | 0.2741 | 0.8851 | 0.471 |
| 3 Stage | | | | |
| 0 | 13100 | 0 | 0 | 0 |
| 15 | 13100 | 0.1528 | 0.1656 | $9.86 \times 10^{-3}$ |
| 30 | 13100 | 0.2661 | 0.2812 | 0.016 |
| 45 | 13100 | 0.3114 | 0.3246 | 0.01 |

TABLE 3

MS/MS TOF, On Axis

| Initial Ion Trajectory Angle (degrees) | Third Electrode Potential (V) | Ion Beam Radial Position (mm) Source Exit | Ion Beam Radial Position (mm) z = 74.4 mm | Spread Angle α (degrees) |
|---|---|---|---|---|
| 2 Stage | | | | |
| 0 | 0 | 0 | 0 | 0 |
| 15 | 0 | 0.1174 | 0.2744 | 0.121 |
| 30 | 0 | 0.1995 | 0.474 | 0.211 |
| 45 | 0 | 0.2311 | 0.545 | 0.242 |
| 3 Stage | | | | |
| 0 | 4900 | 0 | 0 | 0 |
| 15 | 4900 | 0.1528 | 0.1656 | $9.86 \times 10^{-3}$ |
| 30 | 4900 | 0.2661 | 0.2812 | 0.016 |
| 45 | 4900 | 0.3114 | 0.3246 | 0.01 |

TABLE 4

Linear TOF, Off Axis

| Initial Ion Trajectory Angle (degrees) | Third Electrode Potential (V) | Ion Beam Radial Position (mm) Source Exit | Ion Beam Radial Position (mm) z = 74.4 mm | Spread Angle α (degrees) |
|---|---|---|---|---|
| 2 Stage | | | | |
| 0 | 0 | 0.0147 | −0.1042 | −0.119 |
| 15 | 0 | 0.0624 | −0.0933 | −0.12 |
| 30 | 0 | 0.1033 | −0.0798 | −0.141 |
| 45 | 0 | 0.1169 | −0.0757 | −0.148 |
| 3 Stage | | | | |
| 0 | 4400 | 0.0213 | −0.0662 | −0.067 |
| 15 | 4400 | 0.0834 | 0.0032 | $6.20 \times 10^{-2}$ |
| 30 | 4400 | 0.1317 | 0.0461 | −0.066 |
| 45 | 4400 | 0.1523 | 0.0638 | −0.068 |

TABLE 5

Ion Mirror TOF, Off Axis

| Initial Ion Trajectory Angle (degrees) | Third Electrode Potential (V) | Ion Beam Radial Position (mm) Source Exit | Ion Beam Radial Position (mm) z = 74.4 mm | Spread Angle α (degrees) |
|---|---|---|---|---|
| 2 Stage | | | | |
| 0 | 0 | 0.0851 | 0.2388 | 0.118 |
| 15 | 0 | 0.2194 | 0.6869 | 0.36 |
| 30 | 0 | 0.3241 | 1.0062 | 0.525 |
| 45 | 0 | 0.354 | 1.1127 | 0.584 |
| 3 Stage | | | | |
| 0 | 13100 | 0.0994 | 0.0707 | −0.022 |
| 15 | 13100 | 0.2558 | 0.2283 | $-2.10 \times 10^{-2}$ |
| 30 | 13100 | 0.3602 | 0.3412 | −0.015 |
| 45 | 13100 | 0.4037 | 0.3885 | −0.012 |

TABLE 6

| MS/MS TOF, Off Axis | | | | |
|---|---|---|---|---|
| Initial Ion Trajectory Angle (degrees) | Third Electrode Potential (V) | Ion Beam Radial Position (mm) Source Exit | Ion Beam Radial Position (mm) z = 74.4 mm | Spread Angle α (degrees) |
| 2 Stage | | | | |
| 0 | 0 | 0.0454 | 0.0242 | −0.016 |
| 15 | 0 | 0.1603 | 0.2953 | 0.104 |
| 30 | 0 | 0.2434 | 0.4916 | 0.191 |
| 45 | 0 | 0.2752 | 0.5663 | 0.224 |
| 3 Stage | | | | |
| 0 | 4900 | 0.0637 | 0.0128 | −0.039 |
| 15 | 4900 | 0.2164 | 0.1738 | $-3.30 \times 10^{-2}$ |
| 30 | 4900 | 0.3283 | 0.2869 | −0.032 |
| 45 | 4900 | 0.3692 | 0.3304 | −0.03 |

A comparison of the data shows that the angular spread in the ion beam is about an order of magnitude or more lower for the three-stage ion source relative to the two-stage source for all operation modes. In Tables 1-6 the differences tend to be more pronounced for ions formed off the ion optical axis and for ion mirror TOF mode operation.

Figure 6:
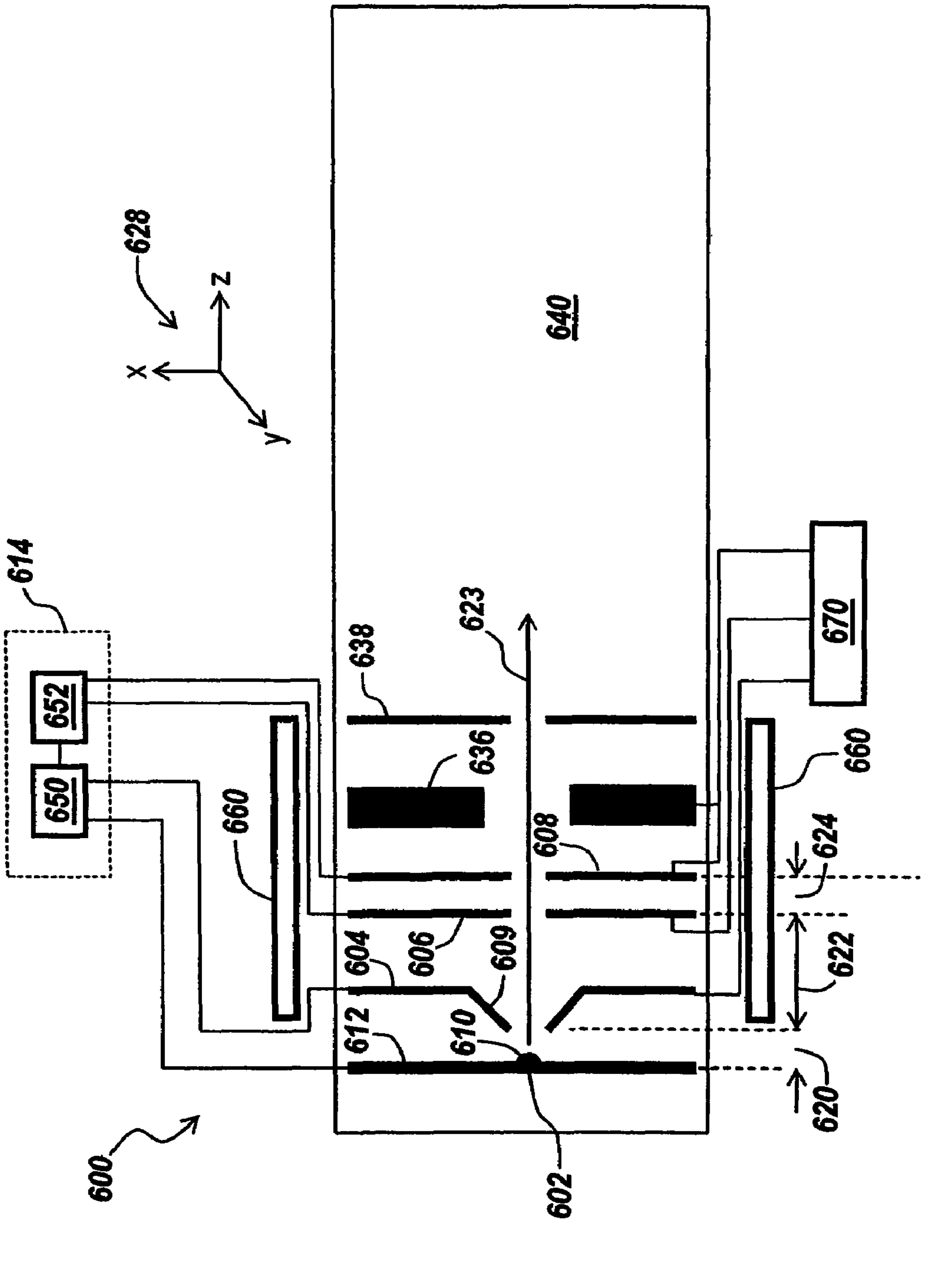
FIG. 6 schematically illustrates various embodiments of a three-stage ion source of the present teachings.

Referring to FIG. 6, in various embodiments a three-field ion source 600 comprises a sample support 602, a first electrode 604, a second electrode 606, and a third electrode 608. A variety of electrode shapes and configurations can be used including, but not limited to, plates, grids, cones, and combinations thereof. For example, the first electrode can be in the form of a skimmer, having a conical portion 609.

Sample ions can be generated by irradiating a sample 610 disposed on a sample surface 612 of the support 602 with a pulse of energy and sample ion energy established by selecting the potential difference between the surface 612 and the third electrode 608. An insulating layer can be interposed between the sample and sample surface. A power source 614, electrically coupled to each of the sample surface 612, first electrode 604, second electrode 606, and third electrode 608, is configured to establish a non-extracting electrical field in a first region 620 that does not substantially accelerate sample ions of interest in a direction away from the sample surface. In various embodiments, the non-extracting electrical field can be a retardation field that retards the motion of the sample ions of interest in a direction away from the sample surface. The power source can, for example, establish an retardation electrical field by applying a first electrical potential to the sample surface and a second electrical potential to the first electrode where: (a) the first electrical potential is more negative than the second electrical potential when the sample ions of interest are positive ions; and (b) the first electrical potential is more positive than the second electrical potential when the sample ions of interest are negative ions. In various embodiments, the non-extracting electrical field can be a substantially zero electrical field, e.g., a substantially electrical field free region is established. An electrical potential applied to one or more of the sample surface, first electrode, and second electrode to establish a non-extracting electrical field can be a zero potential.

The power source is also configured to establish at least in a first region 620 a first extraction electric field at a predetermined time that accelerates sample ions of interest in a first direction 623 away from the sample surface and establish across one or more of the second region 622 and a third region 624 a spatial focus electrical field(s) that spatially focuses sample ions of interest in a direction substantially perpendicular to the first direction 623. The power source can, for example, establish the first extraction electric field by changing the potential on one or more of the sample surface 612, the first electrode 604 and the second electrode 606. An electrical potential applied to one or more of the sample surface, first electrode, second electrode, and third electrode to establish one or more of the first extraction electrical field and the spatial focus electrical field(s) can be a zero potential.

For example, when the sample ions of interest are positive ions the power source can establish a first extraction electrical field by changing the electrical potential on one or more of the sample surface and the first electrode, such that the electrical potential of the sample surface is more positive than the electrical potential of the first electrode; and can establish a second extraction electrical field by establishing a potential difference between the second and third electrodes where the electrical potential on the second electrode is more positive than the electrical potential on the third electrode.

For example, when the sample ions of interest are negative ions the power source can establish a first extraction electrical field by changing the electrical potential on one or more of the sample surface and the first electrode, such that the electrical potential of the sample surface is more negative than the electrical potential of the first electrode; and can establish a second extraction electrical field by establishing a potential difference between the second and third electrodes where the electrical potential on the second electrode is more negative than the electrical potential on the third electrode.

The power source can comprise a single device, multiple stand-alone devices, multiple integrated devices, or combinations thereof. For example, a power source can comprise a first power supply electrically coupled to the sample support and the first electrode, a second power supply electrically coupled to the first electrode and the second electrode, and a third power supply electrically coupled to the second electrode and the third electrode. The power source can be, for example, manually controlled, electronically controlled, and/or programmable.

The term "power source" is used herein to facilitate concise description and is not intended to be limiting. The term "power source" as used herein is not intended to imply that the power source necessarily comprises a single device or that where the power source comprises multiple devices that the sample support, first, second and third electrodes are each electrically coupled to each of the multiple devices. For example, referring again to FIG. 6, in various embodiments a power source 614 can comprise multiple power supplies 650, 652. The power source can be electrically coupled to another power supply, for example, to provide an electrical potential reference, such as, e.g., a floating ground.

In various embodiments, a three-stage ion source of the present teachings includes an optical system configured to irradiate a sample on the sample surface of a sample support with a pulse of laser energy. In various embodiments, the optical system can comprise a lens or window. The optical system can also comprise a mirror or prism to direct the pulse of laser energy onto the sample. In various embodiments, the optical system is configured to substantially align the pulse of laser energy with the direction of ion extraction.

Referring again to FIG. 6, in various embodiments, the three-stage ion source includes a temperature-controlled surface 660 disposed about at least a portion of the source, and a heater system 670 connected to and capable of heating one or more of the first, second and third electrodes. In some embodiments, the heater system 670 is connected to all the elements of the ion source about which the temperature-controlled surface 660 is disposed, the ion optic elements in the path of the neutral beam, or both. In various embodiments, the heater system 670 is connected to the first electrode 604, the second electrode 606, and the third electrode 608.

In various embodiments, a heater system 670 is used to raise the temperature of one or more elements of the ion source to decrease the amount of neutrals deposited on elements of the source. The amount of neutral deposition can be reduced by heating elements of the ion source to, for example, decrease the sticking probability of neutrals on the heated surfaces, volatizing deposits, or both. In various embodiments, a temperature-controlled surface 660 is held at a temperature lower than that of one or more elements of the ion source and is used to capture neutral molecules and prevent their deposition on other surfaces. In various embodiments, the temperature-controlled surface is configured and used to capture neutral molecules and thereby reduce the amount of neutrals deposited on elements of the ion source. The amount of neutral deposition on the ion optics can be reduced by setting the temperature of the temperature-controlled surface lower than that of the elements of the ion source to, for example, increase the sticking probability of neutrals on the temperature controlled surface, capture desorbed neutrals, or both.

In various embodiments, one or more the elements of the ion source are heated such that matrix molecules do not substantially stick to these elements; thereby reducing the buildup of insulating layers on these elements. The neutral plume generated in MALDI can contain a small amount of nonvolatile non-matrix material that can also build up an insulating layer, but the concentration of this non-matrix material is generally several orders of magnitude lower than that of the matrix. This generally results in a much longer time before non-matrix material deposits become significant. In addition, in various embodiments, heating an ion source element surface generally reduces the resistivity of such deposits and thus further facilitates diminishing the effect of asymmetric charging deflecting the ion beam.

In various embodiments, the heater system includes a heater capable of heating the elements of the ion source which are heated to a temperature sufficient to desorb one or more the matrix materials listed in Table 7. The right column of Table 7 lists some of the typical uses for the associated matrix material in MALDI studies.

TABLE 7

| Matrix Material | Typical Uses |
|---|---|
| 2,5-dihydroxybenzoic acid (2,5-DHB) MW 154.03 Da | Peptides, neutral or basic carbohydrates, glycolipids, polar and nonpolar synthetic polymers, small molecules |
| Sinapinic Acid MW 224.07 Da | Peptides and Proteins > 10,000 Da |
| a-cyano-4-hydroxy cinnamic acid (aCHCA) MW 189.04 Da | Peptides, proteins and PNAs < 10,000 Da |
| 3-hydroxy-picolinic acid (3-HPA) MW 139.03 Da | Large oligonucleotides > 3,500 Da |
| 2,4,6-Trihydroxy acetophenone (THAP) MW 168.04 Da | Small oligonucleotides < 3,500 Acidic carbohydrates, acidic glycopeptides |
| Dithranol MW 226.06 Da | Nonpolar synthetic polymers |

TABLE 7-continued

| Matrix Material | Typical Uses |
|---|---|
| Trans-3-indoleacrylic acid (IAA) MW 123.03 Da | Nonpolar polymers |
| 2-(4-hydroxyphenylazo)-benzoic acid (HABA) MW 242.07 Da | Proteins, Polar and nonpolar synthetic polymers |
| 2-aminobenzoic (anthranilic) acid MW 137.05 Da | Oligonucleotides (negative ions) |

In various embodiments, the heater system can raise the temperature of the elements of the ion source which are heated to a temperature sufficient to desorb matrix material.

In various embodiments, the one or more of the elements of the ion source are heated periodically to a sufficiently high temperature to rapidly vaporize any deposits on the surfaces of these elements. In various embodiments, a “blank” or “dummy” sample support is substituted for the MALDI sample support so that the deposits formed, for example, on or more elements of the ion source can be redeposited on the blank (which can be removed from the instrument), the temperature-controlled surface, or both.

In various embodiments, a three-stage ion source of the present teachings includes a fourth electrode. In some embodiments, the fourth electrode is a substantially planar plate or grid that is substantially parallel to the third electrode.

The fourth electrode can be an apertured electrode that is a substantially planar plate or grid. In various embodiments, the fourth electrode is positioned so the centers of the apertures of the second and third apertured electrodes substantially fall on a common axis. In various other embodiments, the fourth electrode is positioned off the axis running through the centers of the apertures in the second and third electrodes. In various embodiments where the fourth electrode is positioned off the axis running through the centers of the apertures in the second and third electrodes, the fourth electrode is positioned such that neutral molecules traveling from the sample support along the extraction direction do not substantially collide with the fourth electrode.

In various embodiments, a three-stage ion source of the present teachings includes a first ion deflector positioned to deflect sample ions in a direction different from the extraction direction. In various embodiments, the first ion deflector is positioned between the third electrode and a fourth electrode. In various embodiments, a fourth electrode is positioned off the axis running through the centers of the apertures in the second and third electrodes such that the fourth electrode can receive deflected sample ions; and in some embodiments, the fourth electrode is positioned such that it facilitates directing sample ions into a mass analyzer.

Ion generation by MALDI produces a plume of neutral molecules in addition to ions. In various embodiments, a portion of this neutral plume passes through apertures in one or more electrodes and forms essentially a cone with an axis substantially along the extraction direction. The size of the aperture in the last electrode and the distance between the last electrode and the sample surface determines the half-angle $\delta$ of the cone about the neutral beam axis that travels beyond the last electrode. In various embodiments where an ion optical element (such as, for example, a fourth electrode) is positioned off the axis running through the centers of the apertures in the second and third electrodes, these ion optical elements can be positioned such that neutral molecules in the neutral beam do not substantially collide with the off-axis ion optical element. In various embodiments, such an off-axis ion optical element is positioned a distance L away from the neutral beam axis in a direction perpendicular to the neutral beam axis. In various embodiments, the off-axis optical element is positioned at a distance L such that the neutral beam intensity at L is at least less than: 14 percent of the neutral beam intensity at the neutral beam axis; 5 percent of the neutral beam intensity at the neutral beam axis; or 1 percent of the neutral beam intensity at the neutral beam axis. In various embodiments, the off-axis ion optical element is positioned such that L is at least a distance $L_{min}$ away where $L_{min}$ can be determined by, $$L_{min}=Dz\tan(\delta), \quad (1)$$

where Dz is the distance in the extraction direction between the off-axis ion optical element and the sample surface, and δ is the half-angle of the neutral beam cone that travels beyond the last element that determines the half-angle δ of the neutral beam cone.

Figure 7A:
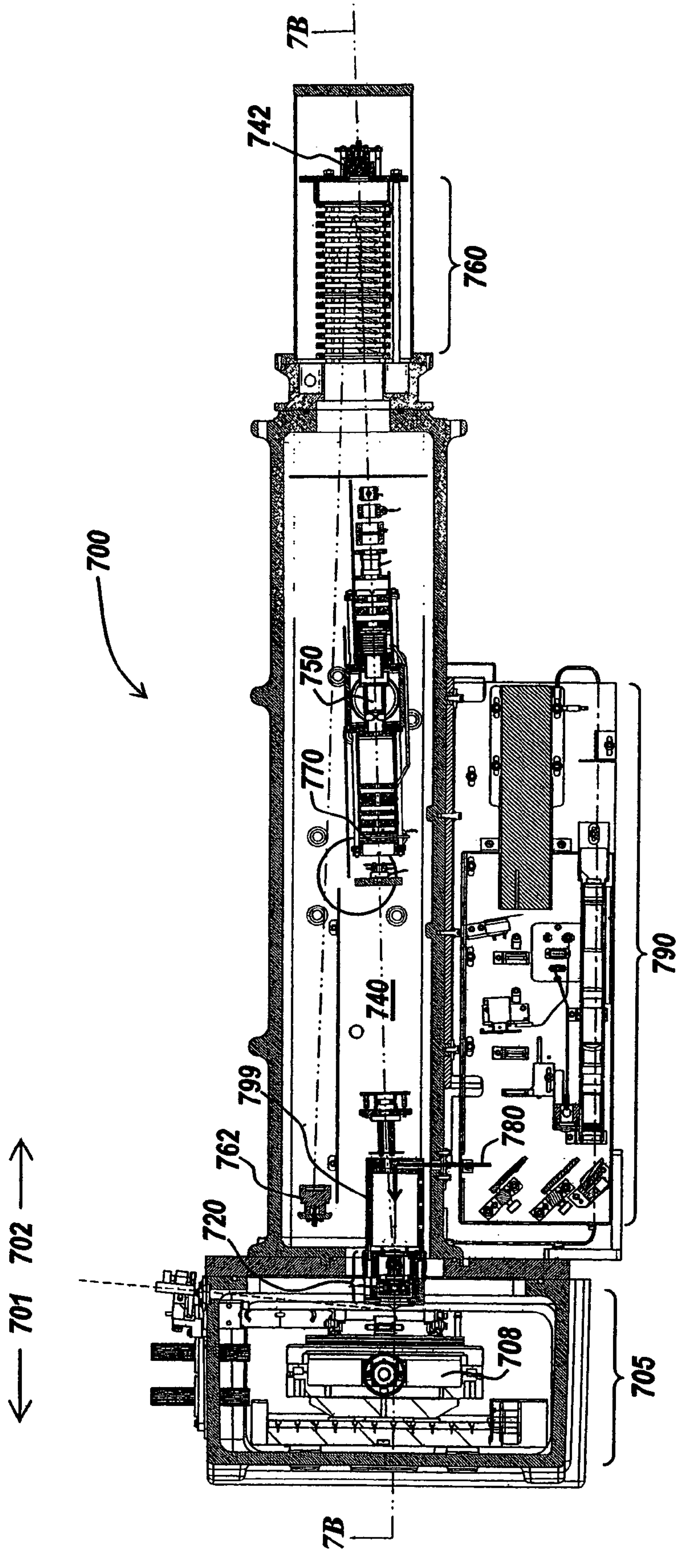
FIGS. 7A and 7B depict sectional views of a MALDI-TOF system incorporating various embodiments of a three-stage ion source of the present teachings.
Figure 7B:
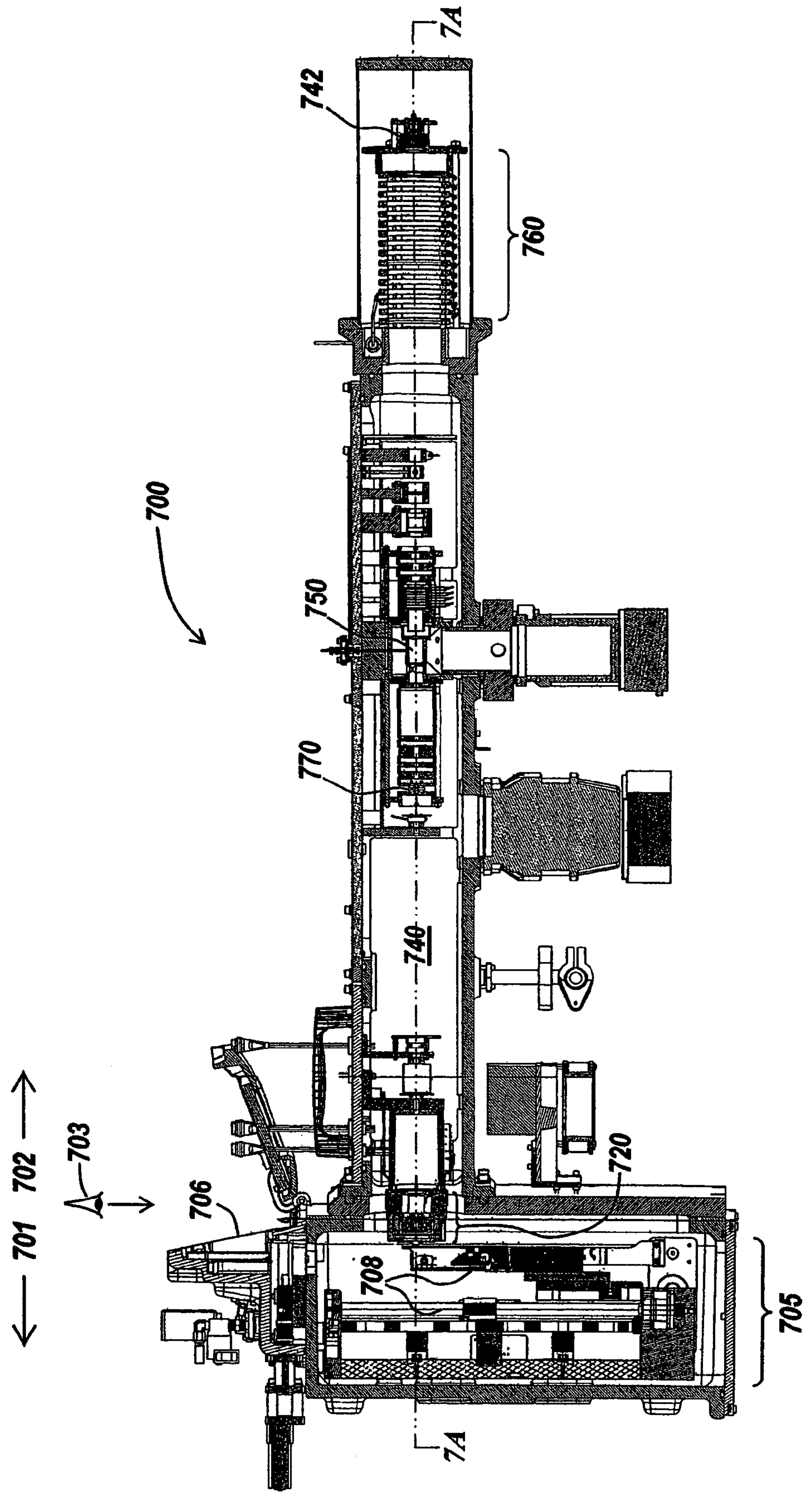
Figure 7C:
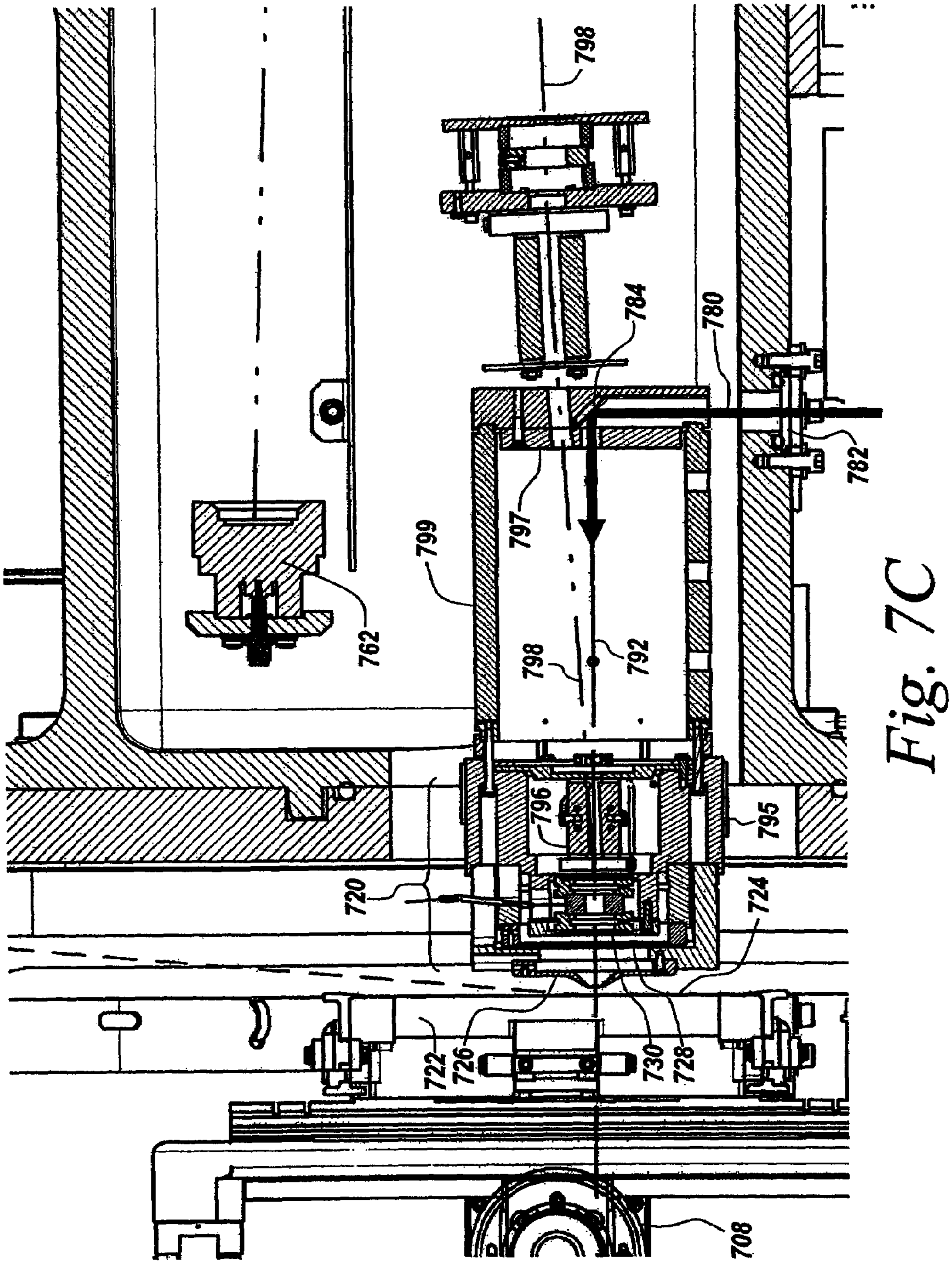
FIG. 7C depicts an expanded view of a portion of FIG. 7A focused on the ion source.

FIGS. 7A and 7B depict substantially to scale views of a MALDI-TOF system 700 incorporating various embodiments of a three-stage ion source of the present teachings. FIG. 7A depicting a front sectional view and FIG. 7B a side sectional view. To facilitate the viewing of FIGS. 7A-7B, the system 700 can be oriented such that the floor is in direction 701, the ceiling in direction 702, and the "front" of the instrument can be considered to be from viewpoint 703. FIG. 7C depicts an expanded view of a portion of FIG. 7A.

The various embodiments illustrated by FIGS. 7A-7C are not intended to be limiting. For example, a MALDI-TOF system incorporating an ion source of the present teachings can comprise fewer system components than illustrated or more system components than illustrated in FIGS. 7A-7C. In addition, the MALDI-TOF systems incorporating an ion source of the present teachings are not necessarily limited to the arrangement of the parts illustrated in FIGS. 7A-7C; rather, the illustrated arrangements are but some of the many modes of practicing the present teachings.

Referring to FIGS. 7A-7C, the illustrated system comprises a sample support handling system 705 comprising a vacuum lock chamber 706, through which sample supports can be loaded and removed, and a sample support transfer mechanism 708 configured to transport sample supports from the vacuum lock chamber 706 to an ion source region 720. The sample support transfer mechanism can comprise a translation mechanism for translating the sample support in one or more dimensions within the ion source region to, for example, facilitate the serial analysis of two or more samples on the sample support. In some embodiments, the translation mechanism comprises an x-y (two dimensions) translational stage.

Referring to FIG. 7C, the ion source region 720 can comprise a three-stage ion source in accordance with the present teachings comprising a sample support 722 having a sample surface 724, a first electrode 726 spaced a part from the sample support 722, a second electrode 728 spaced apart from the first electrode 726 in a direction opposite the sample support 722, and a third electrode 730 spaced apart from the second electrode 728 in a direction opposite the first electrode 726.

In various embodiments, a three-stage ion source can provide an ion beam where the angle of the trajectory at the exit from an acceleration region of the ion source of sample ions substantially at the center of the ion beam is substantially independent of sample ion mass. In some embodiments, such a trajectory is provided by irradiating a sample on a sample surface of a sample support with a pulse of laser energy at an irradiation angle substantially normal to the sample surface and extracting the sample ions in a direction substantially normal to the sample surface to form the ion beam. In various embodiments, the pulse of energy is substantially coaxial with a first ion optical axis substantially parallel to the extraction direction. Examples of irradiation of a sample with a pulse of laser energy at an irradiation angle substantially normal to the sample surface and extraction of the sample ions in a direction substantially normal to the sample surface can be found in U.S. application Ser. No. 10/700,300 filed Oct. 31, 2003, the entire contents of which are herein incorporated by reference.

The system illustrated in FIGS. 7A-7B can be operated in various modes, such as, e.g., linear TOF operation, ion mirror (reflectron) TOF operation, and MS/MS TOF operation. In linear TOF operational mode, ions produced in the ion source region 720 can be extracted (by electrical fields established by one or more ion source electrodes) into a first region substantially free of electrical fields (a first substantially field free region) 740 and drift to a first detector 742. It is to be understood that substantially field free region does not necessarily imply zero-electrical potential rather a substantially constant potential across the region. In linear TOF mode, no gas is added to the collision cell 750 and the ion mirror 760 is off. In linear TOF mode, the time focus plane of the ion source is typically set to coincide with the first detector 742.

In ion mirror (reflectron) mode, ions produced in the ion source region 720 can be extracted (by electrical fields established by one or more ion source electrodes) into the first substantially field free region 740, drift to the ion mirror 760 and are reflected to a second detector 762. As in linear TOF mode, no gas is added to the collision cell 750 in ion mirror TOF mode. In ion mirror TOF mode, the time focus plane of the ion source is typically set to coincide with the focal plane of the ion mirror 760. As a result, the desired position of the time focal plane in ion mirror TOF mode is closer to the ion source than in linear TOF mode operation.

In MS/MS TOF mode, ions produced in the ion source region 720 can be extracted (by electrical fields established by one or more ion source electrodes) into the first substantially field free region 740 and drift to a timed ion selector 770 that selects the parent ion m/z range transmitted to an ion fragmentor (here comprising a collision cell 750) by deflecting away ions outside this m/z range. In MS/MS TOF mode the collision cell 750 can be filled with an appropriate collision gas to fragment parent ions by collision induced dissociation (CID) and produce fragment ions. In various embodiments, fragment ions can be produced from unimolecular dissociation of sample ions, e.g., such unimolecular processes becoming more likely with increasing ion fluence. Fragments ions can be extracted by electrical fields established by one or more exit electrodes into another substantially field free region 772 and fragment ions can be, e.g., analyzed using the ion mirror 760 and detected using the second detector 762, or analyzed without using the ion mirror 760 and detected using the first detector 742. In MS/MS TOF mode, the time focus plane of the ion source is typically set to coincide with the timed ion selector 770. As a result, the desired position of the time focal plane in MS/MS TOF mode is closer to the ion source than in either ion mirror or linear TOF modes of operation.

In various embodiments, a three-stage ion source includes an optical system configured to irradiate a sample on the sample surface 724 of a sample support 722 with a pulse of laser energy 780 at angle substantially normal to the sample surface. In various embodiments, the optical system can comprise a window 782 and a prism or mirror 784 to direct the pulse of laser energy onto the sample. The pulse of laser energy can be provided by a laser system 790, for example, by a pulsed laser or continuous wave (cw) laser. The output of a cw laser can be modulated to produce pulses using, for example, acoustic optical modulators (AOM), crossed polarizers, rotating choppers, and shutters. Any type of laser of suitable irradiation wavelength for producing sample ions of interest by MALDI can be used with the ion sources and mass analyzer systems of the present invention, including, but not limited to, gas lasers (e.g., argon ion, helium-neon), dye lasers, chemical lasers, solid state lasers (e.g., ruby, neodinium based), excimer lasers, diode lasers, and combination thereof (e.g., pumped laser systems).

In various embodiments, a three-stage ion source is configured to extract sample ions in a direction substantially normal to the sample surface. In FIGS. 7A-7C, the ion source includes a first apertured electrode 726 and a second apertured electrode 728. The line between the center of the aperture in the first electrode and the center of the aperture in the second electrode can be used to define a first ion optical axis 792. Accordingly, in various embodiments, a three-stage ion source is configured such that the pulse of radiation and first ion optical axis are substantially coaxial and, in various embodiments, such that the pulse of radiation and first ion optical axis are substantially coincident.

In various embodiments, the aperture in the first electrode is substantially centered on the sample being irradiated by moving the sample support 722. In some embodiments, the sample support 722 is held by a sample support transfer mechanism 794 capable of one-axis translational motion, x-y (2 axis) translational motion, or x-y-z (3 axis) translational motion to position a sample for irradiation. Where the aperture in the first electrode is substantially centered on the sample being irradiated and the first apertured electrode is substantially symmetric about the normal to the sample surface, the extraction direction will be substantially normal to the sample surface.

In some embodiments, the sample support is capable of holding a plurality of samples. Suitable sample supports include, but are not limited to, 64 spot, 96 spot and 384 spot plates. The sample includes a matrix material that absorbs at a wavelength of the pulse of laser energy and which facilitates the desorption and ionization of molecules of interest in the sample.

In various embodiments, a three-stage ion source includes a temperature-controlled surface disposed about at least a portion of the ion source, and a heater system 795 connected to one or more of the first electrode 726, the second electrode 728, the third electrode 730, and a first ion deflector 796. In some embodiments, the heater system is connected to all the ion source elements about which the temperature-controlled surface is disposed, the ion optic system elements in the path of the neutral beam, or both.

In various embodiments, a first ion deflector 796 is positioned between the third electrode 730 and a fourth electrode 797 to deflect sample ions in a direction different from the extraction direction and onto a second ion optical axis 798. A tube or other suitable structure 799 can be used, for example, to shield the sample ions from stray electrical fields, maintain electrical field uniformity, or both, after deflection. In various embodiments, such a structure 799 can serve as a temperature-controlled surface, can be connected to a heater system, or both.

A three-stage ion source of the present teachings may be used with a wide variety of mass analyzers and mass analyzer systems. The mass analyzer can be a single mass spectrometric instrument or multiple mass spectrometric instruments, employing, for example, tandem mass spectrometry (often referred to as MS/MS) or multidimensional mass spectrometry (often referred to as $MS^n$). Suitable mass spectrometers, include, but are not limited to, time-of-flight (TOF) mass spectrometers, quadrupole mass spectrometers (QMS), and ion mobility spectrometers (IMS). Suitable mass analyzers systems can also include ion reflectors and/or ion fragmentors. Examples of suitable mass analyzers and suitable ion fragmentors also include, but are not limited to, those described elsewhere herein.

Examples of suitable ion fragmentors include, but are not limited to, collision cells (in which ions are fragmented by causing them to collide with neutral gas molecules), photodissociation cells (in which ions are fragmented by irradiating them with a beam of photons), and surface dissociation fragmentors (in which ions are fragmented by colliding them with a solid or a liquid surface).

Ion Optics

In various aspects, the present teachings provide methods for focusing ions for an ion fragmentor and methods for operating an ion optical assembly comprising an ion fragmentor. In various embodiments, the present teachings provide methods that substantially maintain the position of the focal point of the an incoming ion beam over a wide range of collision energies, and thereby provide a collimated ion beam for a collision cell over a wide range of energies.

Figure 8A:
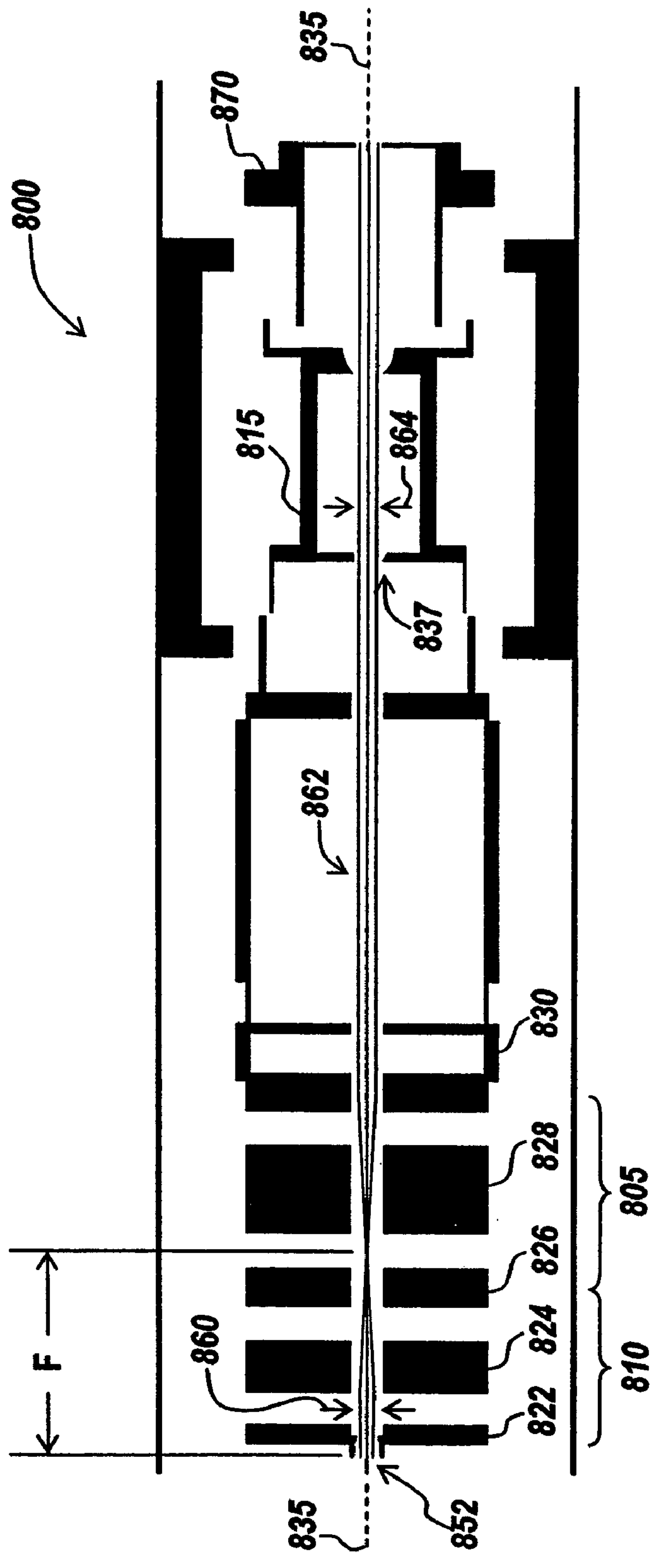
FIG. 8A depicts an ion optical assembly configuration, comprising and ion fragmentor and ion optical elements, and FIG. 8B schematically depicts electrical potentials on various elements of the assembly.
Figure 9:
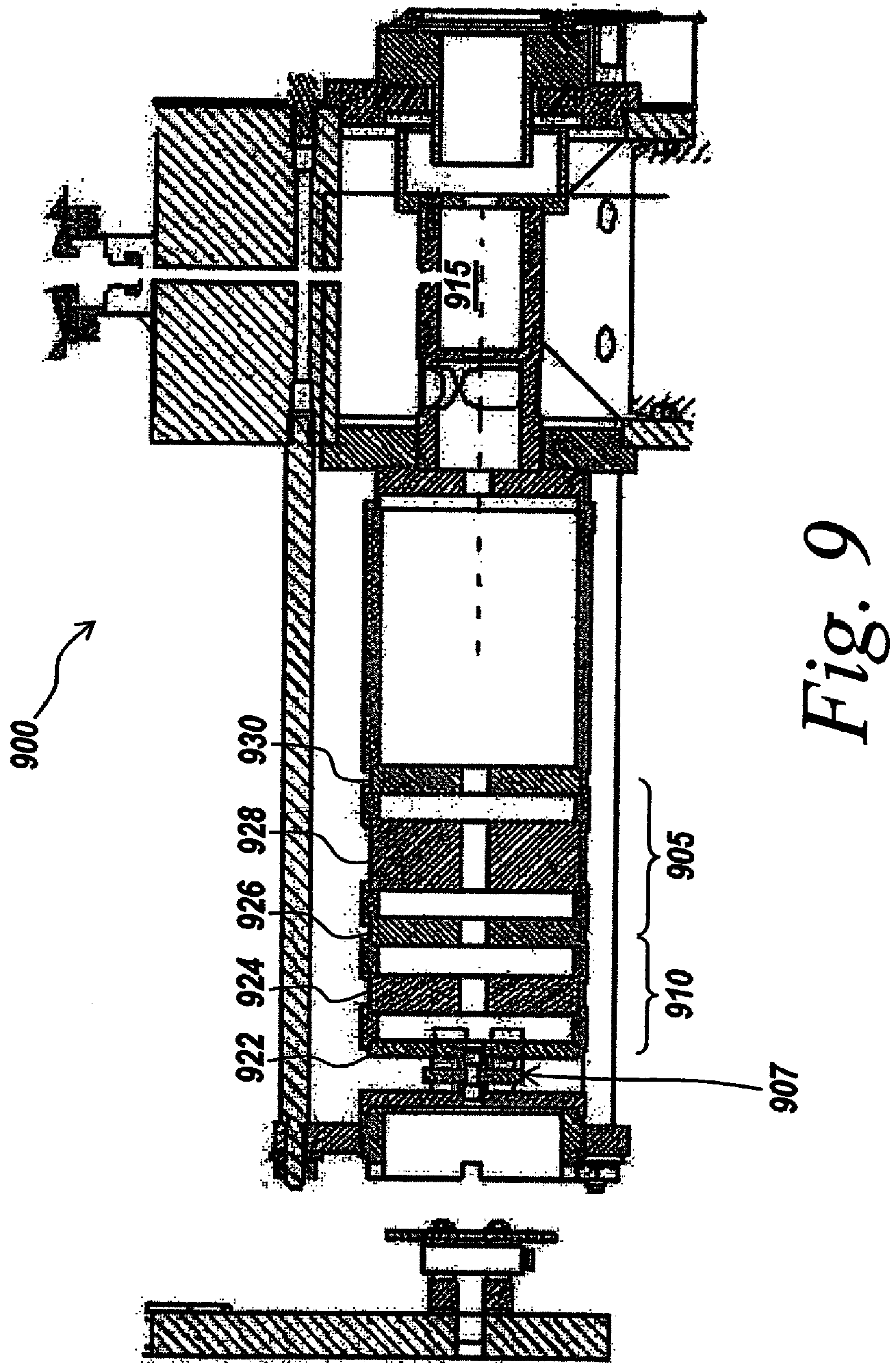
FIG. 9 depicts a sectional of an ion optical assembly comprising and ion fragmentor and ion optical elements.

Referring to FIGS. 8A and 9, in various embodiments, an ion optics assembly 800, 900 comprises a first ion lens 805, 905 disposed between a retarding lens 810, 910 and a collision cell 815, 915. The first ion lens is also referred to herein as a "focus lens" because in various embodiments a radial focal point exists for the ion beam within the first lens. The retarding lens 810, 910 and the focus lens 805, 905 can be composed of multiple lens elements, e.g., electrodes. A variety of electrode shapes and configurations can be used including, but not limited to, plates, grids, cones, and combinations thereof. The ion optics assembly can include a timed ion selector 907 for selecting sample ions for transmittal to the collision cell.

The retarding lens and focus lens can share lens elements. For example, in various embodiments, the retarding lens 810, 910 comprises a first electrode 822, 922, a second electrode 824, 924, and a third electrode 826, 926, and the focus lens 805, 905 comprises the third electrode 826, 926, a fourth electrode 828, 928 and a fifth electrode 830, 930. In various embodiments, various electrodes are at substantially the same potential; for example, in various embodiments, the fifth electrode is at substantially the same potential as the collision cell entrance; in various embodiments, the first electrode is at substantially the same electrical potential as the second electrode; and in various embodiments, the third electrode is at substantially the same electrical potential as the fifth electrode.

Figure 8B:
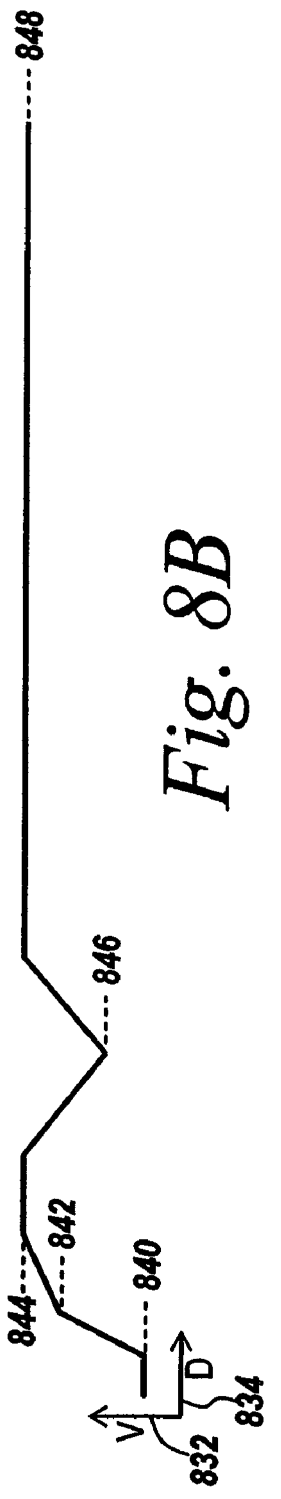

Referring to FIG. 8B, a schematic plot of electrical potential 832 as a function of the direction D 834 along an ion optic axis 835 of the ion optic assembly is illustrated. It should be understood that the absolute and relative values of the electrical potential are not to scale, FIG. 8B being only intended to illustrate whether the electrical potential increases or decreases as one proceeds in the direction D. Further, it should be understood that by typical convention, the electrical potential plot is drawn for the case where the sample ions of interest are positive ions, but that an illustration for negative ions can be had where the electrical potential is viewed as decreasing in the direction V 832.

Referring to FIGS. 8A-9, in various aspects, the present teachings comprise methods for focusing sample ions formed at a source electrical potential. In various embodiments, the methods establish a first electrical field (a decelerating electrical field) with the retarding lens 810, to decelerate incoming sample ions, by applying a first electrical potential to an electrode of the retarding lens; establish a second electrical field (an accelerating electrical field) between the retarding lens 810 and the first ion lens 805 to accelerate sample ions away from the retarding lens and into the first ion lens by applying a second electrical potential to an electrode of the first ion lens; and establish a third electrical field (a decelerating electrical field) between the first ion lens 805 and the entrance 837 to the collision cell to decelerate sample ions prior to entry into the collision cell, by applying a third electrical potential to the entrance of the collision cell.

For example, in various embodiments, a decelerating electrical potential can be applied to the retarding lens 810 by applying to one or more of a first electrode 822 and the second electrode 824 a decelerating electrical potential. For example, positive sample ions entering the retarding lens from a region with at an entry potential 840 (e.g., the electrical potential of a proceeding drift region, ion optical element, etc.) encounter a decelerating potential when the electrical potential of the first electrode 842 and/or the electrical potential of the second electrode 844 is greater than the entry potential 840. Although the electrical potentials on the first and second electrodes are illustrated as different in FIG. 8B, they can be the same. An accelerating electrical potential difference for positive sample ions can be established between the retarding lens 810 and first ion lens 805 by applying an electrical potential 846 to an electrode 828 of the first ion lens which is less than the potential 844 on the retarding lens. A decelerating electrical potential difference for positive sample ions can be established between the first ion lens 805 and the entrance 837 to the collision cell, by applying an electrical potential 848 to the entrance of the collision cell that is greater than the first ion lens potential 846. In various embodiments, various electrodes are at substantially the same potential; for example, in various embodiments, the third electrode, the fifth electrode and the collision cell entrance are at substantially the same electrical potential 848.

In various embodiments, sample ions are substantially focused to a focal point a distance F from an entrance 852 to the retarding lens 810, 910. In various embodiments, the methods maintain the focal point of a collimated input ion beam at substantially the same position in the ion optic assembly over a range of collision energies by changing the electrical potential on the focus lens 805. In various embodiments, when the difference between a first collision energy and a second collision energy is less than about 5000 electron volts, the distance F varies within less than about: (a) ±4%; (b) ±2%; and/or (c) ±1%.

Table 8 presents data on the position of the focal point at two different collision energies 500 electron volts (eV) and 1000 eV for a collimated input ion beam with an input diameter 860 focused to a focal point a distance F from the entrance 852 and forming a collimated ion beam 862 with an output diameter 864. In FIG. 8A, electrical potentials applied to an ion optical element 870 after the collision cell 815. Referring to Table 8, it can be seen that the calculated position of the focal point changes by less than 1% upon changing the collision energy from 500 eV to 1000 eV and changing the electrical potentials on the retarding lens 810 and the focus lens in accordance with the present teachings.

Figure 10A:
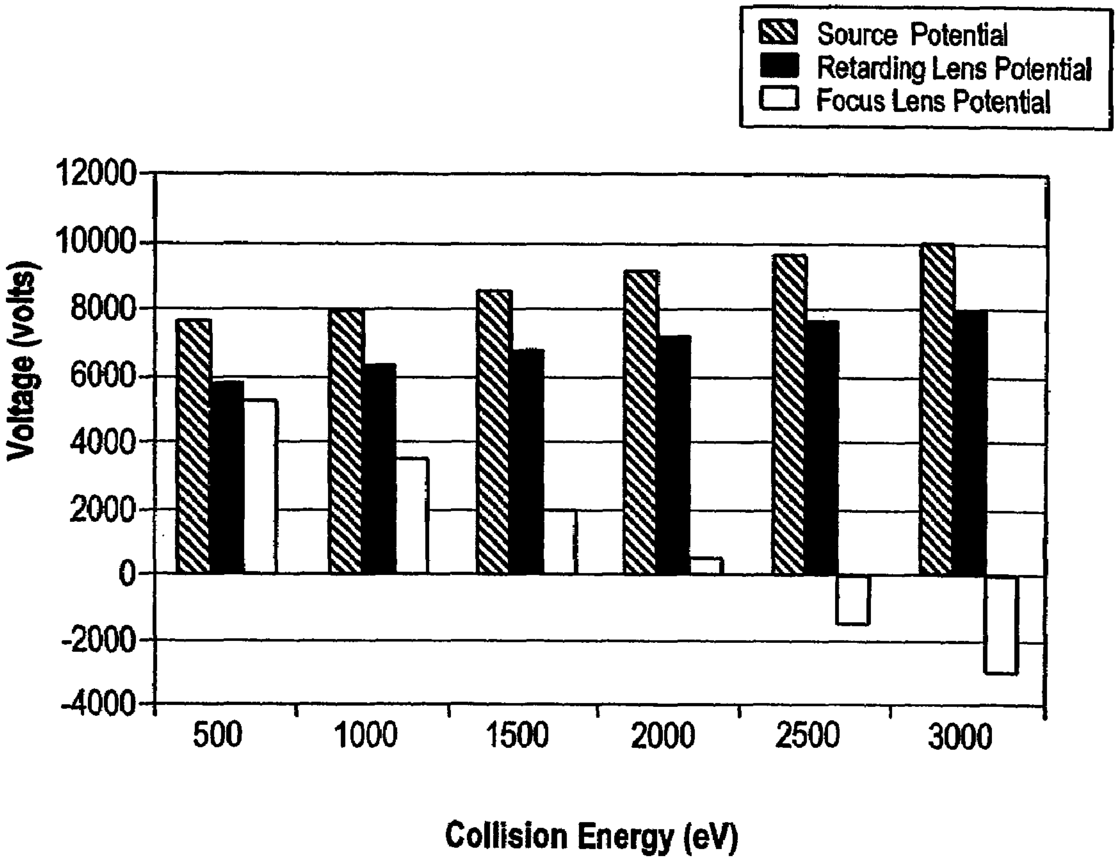
FIGS. 10A-10B are bar graphs illustrating the potentials on various ion optics at different collision energies for the ion optical assembly of FIG. 8A.

Table 9 and FIG. 10A present data on the calculated electrical potentials for application to the retarding lens 810 and the focus lens 805 which maintain the focal point at a distance F substantially equal to 34 mm over a range of collision energies in accordance with various embodiments of the present teachings.

Figure 10B:
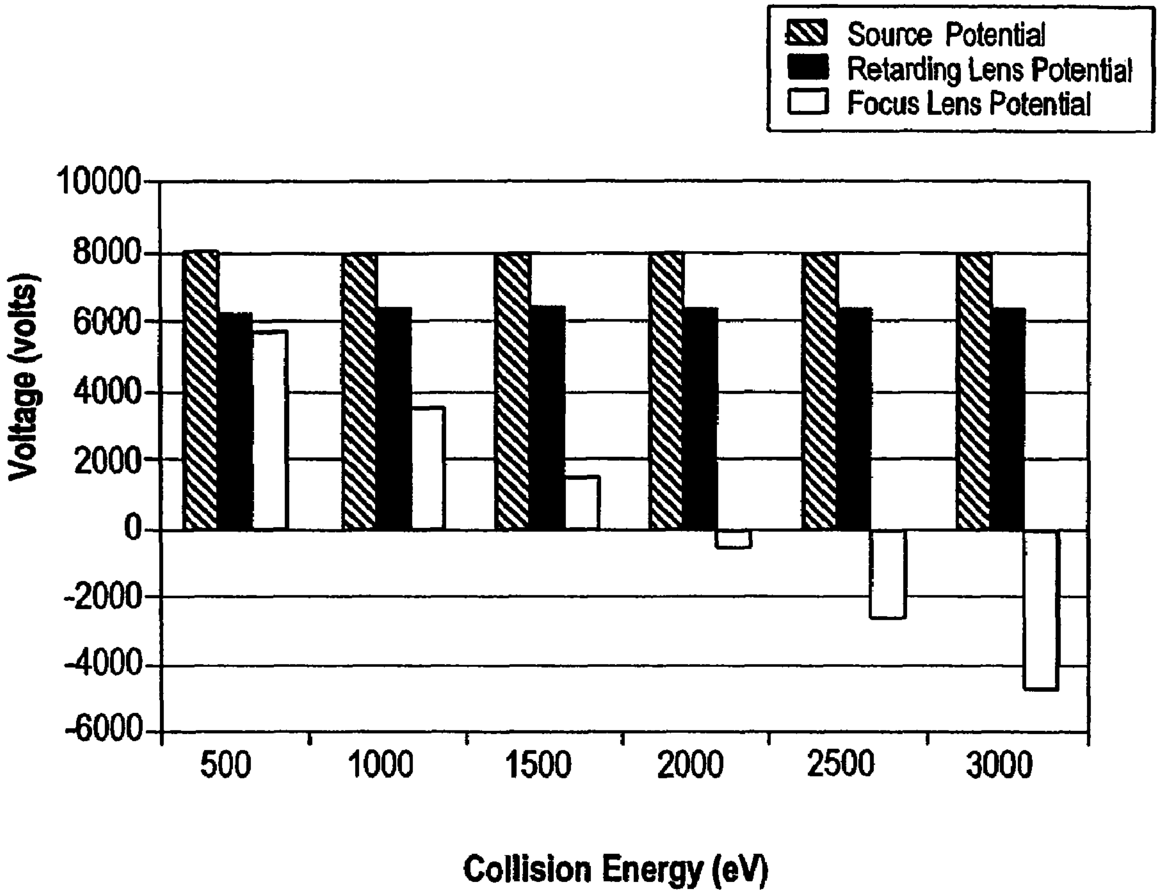

Table 10 and FIG. 10B present data on the calculated electrical potentials for application to the retarding lens 810 and the focus lens 805 which maintain the focal point at a distance F substantially equal to 34 mm over a range of collision energies in accordance with various embodiments of the present teachings where the focal point is maintained substantially at the distance F=34 mm by substantially maintaining the electrical potential on the retarding ion lens 810 and changing the electrical potential on the first ion lens 805. For example, for the 500 eV collision energy data the retarding ion lens potential (6200 V) is within less than 2.5% of potential applied (6350 V) at the other collision energies.

The data of Tables 8, 9 and 10 and FIGS. 10A and 10B was calculated using SIMION (v7.0, Idaho National Engineering and Environmental Laboratory) where input and output parameters are listed in the tables. Tables 9 and 10, respectively, provide the values plotted in FIGS. 10A and 10B. The structure used for the SIMION calculations was substantially that shown in FIG. 8A, where the structural elements are substantially to scale. Estimates of the absolute size of the structure in FIG. 8A can be made by noting that the distance between the entrance to the first electrode 822 and the focal point distance F is about 34 mm as illustrated in FIG. 8A.

It is to be understood that although electrical potentials are given in Tables 8-10 and FIGS. 10A-10B, that the absolute values of the potentials are not critical to the present teachings. Further, it is to be understood that where various electrical potentials are noted as zero or ground, this is purely for convenience of notation and conciseness herein. One of skill in the art will readily recognize that it is not necessary to the present teachings that the potential at an electrode be at a true earth ground electrical potential. For example, the potential at the electrode can be a "floating ground" with an electrical potential significantly above (or below) true earth ground (e.g., by thousands of volts or more). Accordingly, the description of an electrical potential as zero or as ground herein should not be construed to limit the value of an electrical potential with respect to earth ground in any way.

TABLE 8

Focal Point Position and Ion Beam Diameter

| | 1000 eV Collision Energy | 500 eV Collision Energy |
|---|---|---|
| mass (Da) | 1000 | 1000 |
| source potential (V) | 8000 | 7500 |
| retarding lens: second electrode potential (V) | 6300 | 5750 |
| focus lens: fourth electrode potential (V) | 3500 | 5250 |
| collision cell entrance potential (V) | 7000 | 7000 |
| retarding focal point F (mm) | 34.0 | 34.3 |
| ion beam diameter at entrance (mm) | 2.1 | 2.1 |
| ion beam diameter at exit (mm) | 3.8 | 4.3 |

TABLE 9

| Source Potential Varied, Collision Cell Potential Constant at 7000 V | | | |
|---|---|---|---|
| Collision Energy (eV) | Source Potential (V) | Retarding Lens Second Electrode Potential (V) | Focus Lens Fourth Electrode Potential (V) |
| 500 | 7500 | 5750 | 5250 |
| 1000 | 8000 | 6300 | 3500 |
| 1500 | 8500 | 6700 | 2000 |
| 2000 | 9000 | 7100 | 500 |
| 2500 | 9500 | 7500 | −1500 |
| 3000 | 10000 | 7875 | −3000 |

TABLE 10

| Source Potential Constant at 8000 V, Collision Cell Potential Varied | | | |
|---|---|---|---|
| Collision Energy (eV) | Collision Cell Entrance Potential (V) | Retarding Lens Second Electrode Potential (V) | Focus Lens Fourth Electrode Potential (V) |
| 500 | 7500 | 6200 | 5700 |
| 1000 | 7000 | 6350 | 3500 |
| 1500 | 6500 | 6350 | 1500 |
| 2000 | 6000 | 6350 | −500 |
| 2500 | 5500 | 6350 | −2500 |
| 3000 | 5000 | 6350 | −4500 |

Ion Optical Assemblies

Figure 11:
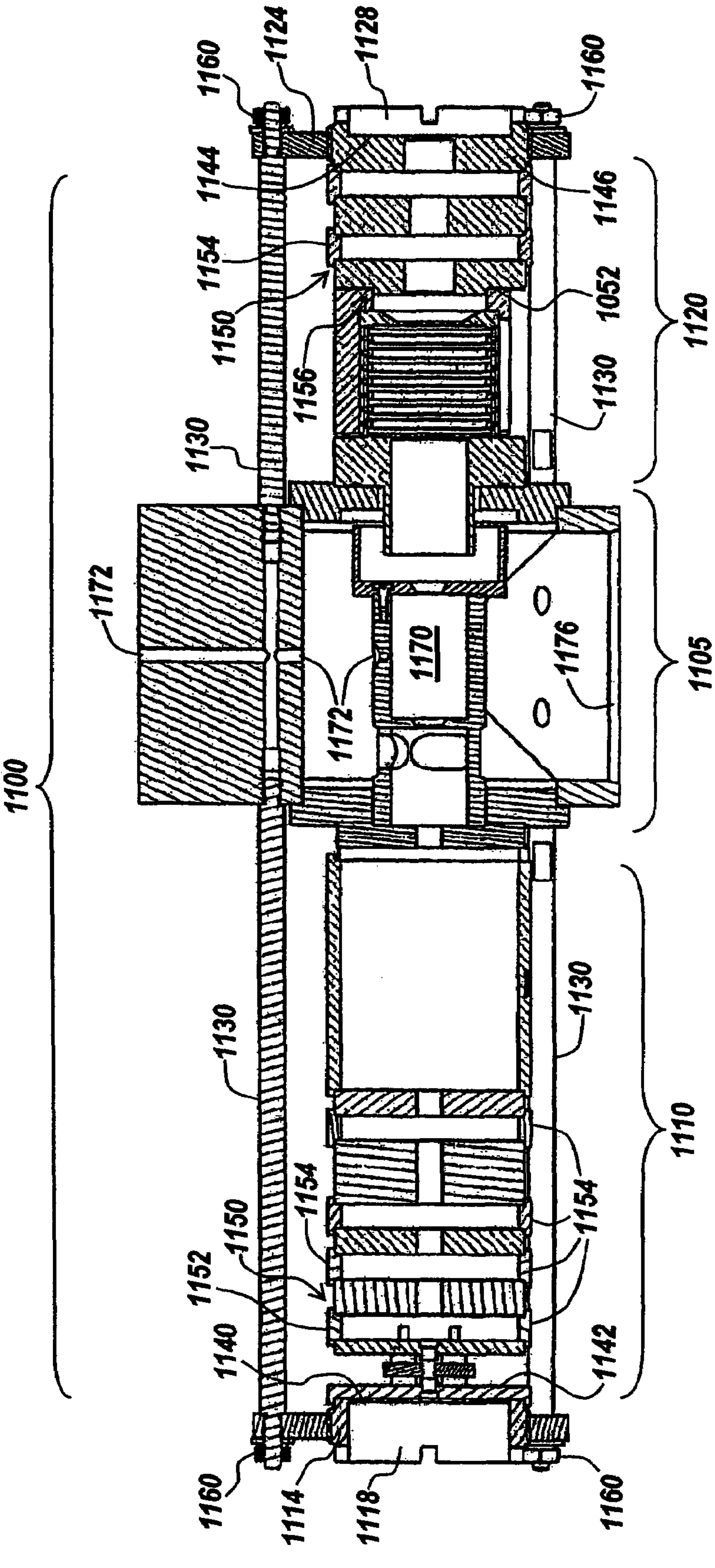
FIG. 11 depicts a side sectional view of various embodiments of ion optical assemblies of the present teachings.
Figure 12:
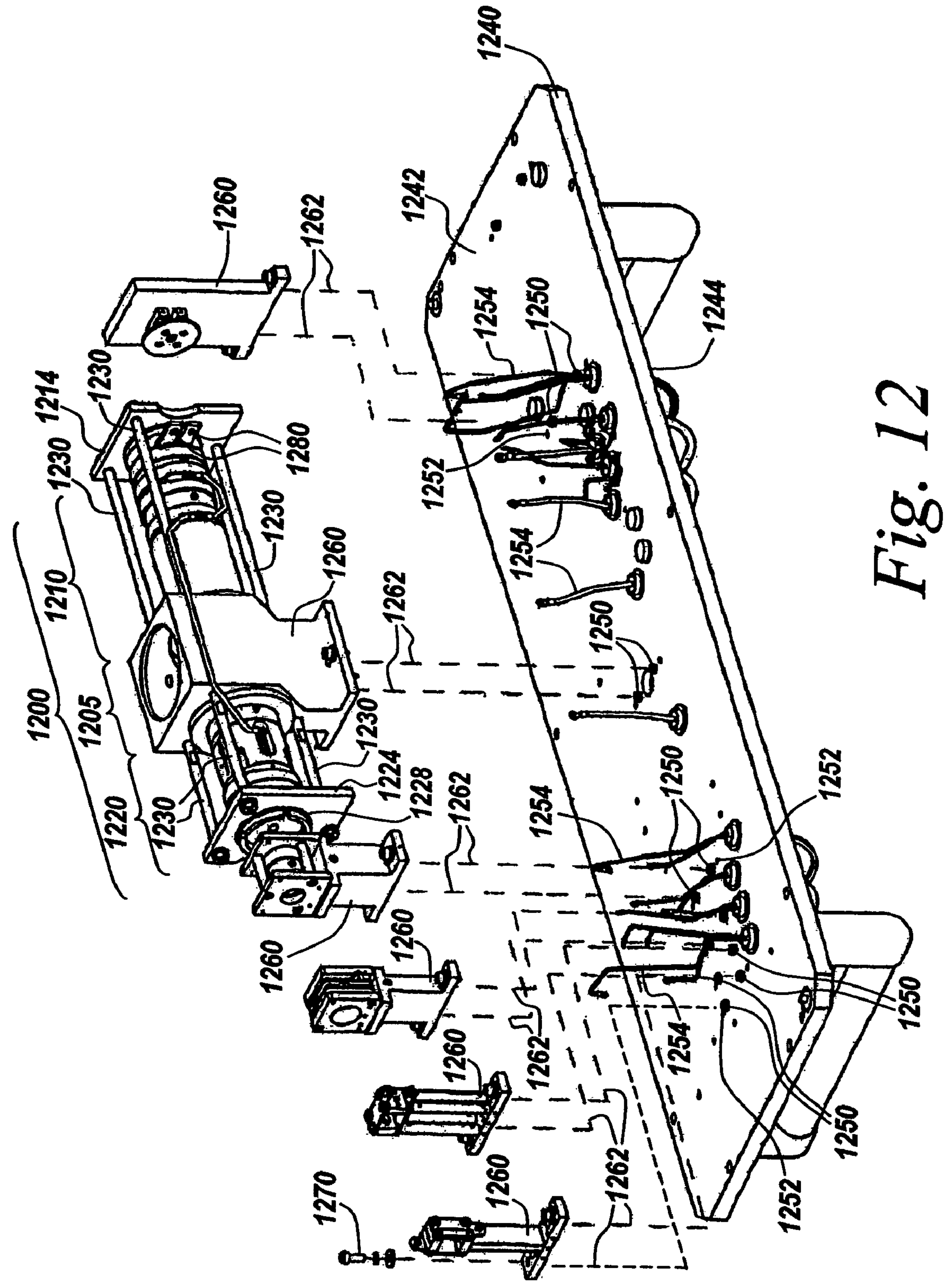
FIG. 12 depicts an isometric view of various embodiments of systems for mounting and aligning ion optic components of the present teachings.

In various aspects, the present teachings provide ion optical assemblies with features that facilitate the alignment of ion optical elements. Referring to FIGS. 11 and 12, in various embodiments, an ion optics assembly 1100, 1200 of the present teachings comprises a mounting body 1105, 1205, a first plurality of ion optical elements 1110, 1210, a front member 1114, 1214, a front securing member 1118, (obscured by the front member in FIG. 12), second plurality of ion optical elements 1120, 1220, a back member 1124, 1224, and a back securing member 1128, 1228. The front member 1114, 1214 and back member 1124, 1224 are attached to the mounting body 1105 by at least one attachment member 1130, 1230.

The end members (front member 1114, 1214 and back member 1124, 1224) are threaded such that when their associated securing members (front 1118 and back 1128, 1228, respectively) are engaged in them, a contact face of the securing member can contact an ion optical element of the associated plurality of elements (e.g., a front member contact face 1140 contacting an element 1142 of the first plurality, and a back member contact face 1144 contacting an element 1146 of the second plurality) and apply a compressive force against the plurality of ion optical elements.

In various embodiments, each ion optical element comprises a recess structure adapted to receive a complimentary registration structure, the registration structure aligning an ion optical element with respect its neighbors when said registration structure is registered in the complimentary recess structure when a compressive force is applied by the respective securing member.

For example, a recess structure 1150 can comprise, e.g., a slot, counter-bore, hole, etc., configured to receive a complimentary registration structure, e.g., a pin, spacer, etc., a recess structure 1152 can comprise a first surface intersecting the face of the ion optical element to form, e.g., a corner on the face of the element against which a neighboring ion optical element can register. In various embodiments, a registration structure can serve as a spacer 1154 (which can be electrically insulating) to properly space ion optical elements. In various embodiments, the registration structure is provided by the shape of the ion optical element, such as, e.g., a corner 1156 that can register against a corner on the face of a neighboring element.

In the present teachings, ion optical elements are aligned by applying a compressive force with the respective securing member. The compressive force is applied by engaging the thread on the securing member with those on the respective end member. As used herein, the terms "threads" and "threaded" include, but are not limited to helical ridges, spiral ridges and circular ridges. Accordingly, these terms include, but are not limited to, parallel ridges that form complete circles or segments of a complete circle. The ridges can be continuous or interrupted. For example the ridges can be cut to facilitate pumping out gas trapped or out gassed in these spaces.

In various embodiments where the threads comprise helical or spiral ridges, the securing member can be screwed into the respective end member to apply the compressive force. In various embodiments where the threads comprise circular ridges, the securing member is pushed into the respective end member (e.g., providing a snap fit) to apply the compressive force. In various embodiments, the securing members are self locking, which can, e.g., help prevent an ion optics lens stack from loosening due to shipping or instrument vibration. In various embodiments, the securing members are self-locking when a pre-selected torque is applied. In various embodiments, the securing members are self-locking when pushed in (e.g., giving a snap fit), which can also include turning the securing member, e.g., to rotate a structure on securing member (which passed through a cut in a thread when pushed in) to a position behind a thread, locking the securing member in place.

The end members can be attached to the mounting body by any suitable means. The attachments can be permanent or reversible. FIG. 11 provides a non-limiting example of one attachment means, but those of ordinary skill in the art will recognize that many other means are available. For example, in various embodiments, the end members are attached using threaded rods one end of which is pushed or screwed into the mounting body and another which is attached to the end member by means of bolts.

In various embodiments, the mounting body comprises a region for performing ion fragmentation. For example, in various embodiments, the mounting body comprises a collision cell 1170 having, e.g., a channel 1172 for the provision of a collision gas, and an opening 1176 for fluid communication with a vacuum pump.

In various embodiments, the alignment of the ion optical elements by compressing them with the securing members, as described in the present teachings, can simplify the alignment and assembly of ion optical elements. In the present teachings, no torque pattern is required to compress and align the ion optical elements. In various embodiments, the securing members can lock the ion optics elements in place, so no additional parts are required to secure the ion optic assembly for shipping.

In various aspects, the present teachings provide systems for mounting and aligning ion optic components. Referring to FIG. 12, in various embodiments, a mounting and aligning system comprises a mounting base 1240 having a mounting surface 1242 and a back surface 1244 opposite the mounting surface. A plurality of pairs of protrusions 1250 protrude from the mounting surface 1242, one or more mounting structures 1252 are associated with each pair of protrusions and at least one electrical connection element 1254 is associated with each pair of protrusions, where the element connection elements pass through the mounting base from the back surface to the mounting surface. The system also comprises two or more ion optic component supports 1260, each ion optic component support having a pair of recesses configured to receive one or more of the plurality of pairs of protrusions (the general location of each recess on the face of ion optic component support brought in contact with the mounting surface is indicated by a dashed line 1262 connecting to the corresponding protrusion).

The positions of the pairs of protrusions on the mounting surface and their corresponding recesses are configured such that when the pair of recesses of an ion optic component support is brought into registration with the corresponding pair of protrusions by mounting an ion optic component to the mounting base using the one or more mounting structures associated with the pair of protrusions (e.g., using bolts 1270 to mount into a threaded hole mounting structure 1252), an ion optics component mounted in said ion optic component support is substantially aligned with other ion optics components so mounted and an electrical connection site (e.g., 1280) on said ion optics component is proximate to a corresponding electrical connection element associated with the corresponding pair of protrusions.

A wide variety of protrusion and complimentary recess shapes can be used, including but not limited to pins mating to holes and/or slots. In various embodiments, the plurality of pairs of protrusions are configured such that only one orientation of an ion optic component support will enable the pair of recesses of the ion optic component support to be brought into registration with the corresponding pair of protrusions. For example, in various embodiments, unique recess and protrusion patterns can be used to orient an ion optic component support. In various embodiments, the pairs of protrusions are configured to have different shapes for different ion optic components.

Mass Analyzer Systems

In various aspects, the present teachings provide MALDI-TOF mass analyzer systems. Referring to FIGS. 1A-1D, 2, 3 and 7A-7C, in various embodiments, a mass analyzer system comprises: (a) an optical system 782, 784 configured to irradiate a sample 370 on a sample surface 192, 375 with a pulse of energy 165 such that the pulse of energy strikes a sample on the sample surface at an angle substantially normal to the sample surface; (b) a MALDI ion source 720 of the present teachings; (c) an ion deflector 796 configured to deflect ions from a first ion optical axis 166, 792 along which ions are extracted into the mass analyzer system and onto a second ion optical axis 194, 798; (d) a first substantially field free region 120, 740 positioned between the ion deflector 796 and a timed ion selector 142, 770, the timed ion selector being positioned between the first substantially field free region and a collision cell 144, 750; (e) a second substantially field free region 122 positioned between the collision cell and a first ion detector 125; (f) an ion mirror 130 positioned between the second substantially field free region and the first ion detector; and (g) a third substantially field free region 124 positioned between the ion mirror and a second ion detector 135. The timed ion selector is positioned to receive ions traveling along the second ion optical axis and is configured to select ions for transmittal to the collision cell.

In various embodiments, the optical system can comprise a window 782 and a prism or mirror 784 to direct the pulse of laser energy onto the sample. In various embodiments, one or more structures 190 can be provided, for example, to shield the sample ions from stray electrical fields, maintain electrical field uniformity, or both, as they travel from the ion mirror 130 to the second detector 135.

In various embodiments, the MALDI ion source 720 comprises a first electrode 726 spaced apart from the sample support 722; a second electrode 728 spaced apart from the first electrode in a direction opposite the sample support holder; and a third electrode 730 spaced apart from the second electrode in a direction opposite the first electrode; where a power source is electrically coupled to the sample support, the first electrode, the second electrode, and the third electrode and configured to: apply a first potential to the sample surface and a second potential to at least one of the first electrode and the second electrode to establish a non-extracting electric field at a first predetermined time substantially prior to striking a sample on the sample surface with a pulse of energy to form sample ions, the non-extracting electrical field substantially not accelerating sample ions in a direction away from the sample surface; change the electrical potential of at least one of the sample surface and the first electrode to establish a first extraction electric field at a second predetermined time subsequent to the first predetermined time, the first extraction electric field accelerating sample ions in a first direction away from the sample surface, the first extraction electric field accelerating sample ions in a first direction away from the sample surface along a first ion optical axis that is substantially coaxial with the pulse of energy; and apply a third potential to the second electrode to focus ions in a direction substantially perpendicular to the first direction.

In various embodiments, a mass analyzer system further comprises a vacuum lock chamber 106 and a sample chamber 160 connected to the vacuum lock chamber. A sample support changing mechanism 210 is disposed in the vacuum lock chamber and a sample support transfer mechanism 108 is disposed in the sample chamber. The sample support transfer mechanism configured to extract a sample support from a loading region 220 of the sample support changing mechanism such that the sample support is registered within a frame 310 in the sample support transfer mechanism. The sample support transfer mechanism is mounted on a multi-axis translation stage 112 such that the sample support can be translated to a position where sample ions can be generated by laser irradiation of a sample on the surface of the sample support by a pulse of energy 164 while said sample support is held in the sample support transfer mechanism and the sample support transfer mechanism is in the sample chamber, and said sample ions extracted along the first ion optical axis 166, 792.

In various embodiments, the non-extracting electrical field can be a retardation electrical field which retards the motion of sample ions in a direction away from the sample surface. In various embodiments, the non-extracting electrical field can be a substantially zero electrical field, e.g., a substantially electrical field free region is established. A substantially zero electrical field can be established, e.g., when the first potential and the second potential are substantially equal.

In various embodiments, a mass analyzer system further comprises one or more temperature controlled surfaces disposed therein.

In various embodiments, the timed ion selector 142, 770 and the collision cell comprise 144, 750 portions of an ion optical assembly 195, the ion optical assembly comprising a first plurality of ion optical elements 196 disposed between a front member 197 and a front side of a mounting body 198. The front member is attached to the mounting body by at least one attachment member 199 and the front member has a threaded opening configured to accept a threaded surface of a front securing member. The mounting body contains the collision cell and the timed ion selector comprises at least one of the ion optical elements. The threaded opening of the front member is configured such that when the threaded surface of the front securing member is engaged in the threaded opening of the front member, a contact face of the front securing member can contact an ion optical element of the first plurality and apply a compressive force against the first plurality of ion optical elements. Each ion optical element of the first plurality has a recess structure adapted to receive a complimentary registration structure, a registration structure aligning an ion optical element of the first plurality with respect to at least one other ion optical element of the first plurality when the registration structure is registered in a complimentary recess structure when the compressive force is applied by the front securing member.

Ion generation by MALDI produces a plume of neutral molecules in addition to ions. In various embodiments where an ion optical element is positioned off the axis running through the centers of the apertures in the first ion optical axis 166, 792, these optical elements can be positioned such that neutral molecules in the neutral beam do not substantially collide with the off-axis ion optical element. In various embodiments, such an off-axis ion optical element is positioned a distance L away as can be determined by Equation (1).

Mass Analyzers

A wide variety of mass analyzers may be used with various aspects of the present teachings. The mass analyzer can be a single mass spectrometric instrument or multiple mass spectrometric instruments, employing, for example, tandem mass spectrometry (often referred to as MS/MS) or multidimensional mass spectrometry (often referred to as $MS^n$). Suitable mass spectrometers, include, but are not limited to, time-of-flight (TOF) mass spectrometers, quadrupole mass spectrometers (QMS), and ion mobility spectrometers (IMS). Suitable mass analyzers systems can also include ion reflectors and/or ion fragmentors.

Examples of suitable ion fragmentors include, but are not limited to, collision cells (in which ions are fragmented by causing them to collide with neutral gas molecules), photodissociation cells (in which ions are fragmented by irradiating them with a beam of photons), and surface dissociation fragmentors (in which ions are fragmented by colliding them with a solid or a liquid surface).

In various embodiments, the mass analyzer comprises a triple quadrupole mass spectrometer for selecting a primary ion and/or detecting and analyzing fragment ions thereof. In various embodiments, the first quadrupole selects the primary ion. The second quadrupole is maintained at a sufficiently high pressure and voltage so that multiple low energy collisions occur causing some of the ions to fragment. The third quadrupole is scanned to analyze the fragment ion spectrum.

In various embodiments, the mass analyzer comprises two quadrupole mass filters and a TOF mass spectrometer for selecting a primary ion and/or detecting and analyzing fragment ions thereof. In various embodiments, the first quadrupole selects the primary ion. The second quadrupole is maintained at a sufficiently high pressure and voltage so that multiple low energy collisions occur causing some of the ions to fragment, and the TOF mass spectrometer detects and analyzes the fragment ion spectrum.

In various embodiments, a mass analyzer for use with the present teachings comprises two TOF mass analyzers and an ion fragmentor (such as, for example, CID or SID). In various embodiments, the first TOF selects the primary ion for introduction in the ion fragmentor and the second TOF mass spectrometer detects and analyzes the fragment ion spectrum. The TOF analyzers can be linear or reflecting analyzers.

In various embodiments, the mass analyzer comprises a time-of-flight mass spectrometer and an ion reflector. The ion reflector is positioned at the end of a field-free drift region of the TOF and is used to compensate for the effects of the initial kinetic energy distribution by modifying the flight path of the ions. In various embodiments ion reflector consists of a series of rings biased with potentials that increase to a level slightly greater than an accelerating voltage. In operation, as the ions penetrate the reflector they are decelerated until their velocity in the direction of the field becomes zero. At the zero velocity point, the ions reverse direction and are accelerated back through the reflector. The ions exit the reflector with energies identical to their incoming energy but with velocities in the opposite direction. Ions with larger energies penetrate the reflector more deeply and consequently will remain in the reflector for a longer time. The potentials used in the reflector are selected to modify the flight paths of the ions such that ions of like mass and charge arrive at a detector at substantially the same time.

In various embodiments, the mass analyzer comprises a tandem MS-MS instrument comprising a first field-free drift region having a timed ion selector to select a primary sample ion of interest, a fragmentation chamber (or ion fragmentor) to produce sample ion fragments, a mass analyzer to analyze the fragment ions. In various embodiments, the timed ion selector comprises a pulsed ion deflector. In various embodiments, the second ion deflector can be used as a pulsed ion deflector in versions of this tandem MS/MS instrument. In various embodiments of operation, the pulsed ion deflector allows only those ions within a selected mass-to-charge ratio range to be transmitted to the ion fragmentation chamber. In various embodiments, the mass analyzer is a time-of-flight mass spectrometer. The mass analyzer can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In various embodiments, the mass analyzer comprises a tandem TOF-MS having a first, a second, and a third TOF mass separator positioned along a path of the plurality of ions generated by the pulsed ion source. The first mass separator is positioned to receive the plurality of ions generated by the pulsed ion source. The first mass separator accelerates the plurality of ions generated by the pulsed ion source, separates the plurality of ions according to their mass-to-charge ratio, and selects a first group of ions based on their mass-to-charge ratio from the plurality of ions. The first mass separator also fragments at least a portion of the first group of ions. The second mass separator is positioned to receive the first group of ions and fragments thereof generated by the first mass separator. The second mass separator accelerates the first group of ions and fragments thereof, separates the first group of ions and fragments thereof according to their mass-to-charge ratio, and selects from the first group of ions and fragments thereof a second group of ions based on their mass-to-charge ratio. The second mass separator also fragments at least a portion of the second group of ions. The first and/or the second mass separator may also include an ion guide, an ion-focusing element, and/or an ion-steering element. In various embodiments, the second TOF mass separator decelerates the first group of ions and fragments thereof. In various embodiments, the second TOF mass separator includes a field-free region and an ion selector that selects ions having a mass-to-charge ratio that is substantially within a second predetermined range. In various embodiments, at least one of the first and the second TOF mass separator includes a timed-ion-selector that selects fragmented ions. In various embodiments, at least one of the first and the second mass separator includes an ion fragmentor. The third mass separator is positioned to receive the second group of ions and fragments thereof generated by the second mass separator. The third mass separator accelerates the second group of ions and fragments thereof and separates the second group of ions and fragments thereof according to their mass-to-charge ratio. In various embodiments, the third mass separator accelerates the second group of ions and fragments thereof using pulsed acceleration. In various embodiments, an ion detector positioned to receive the second group of ions and fragments thereof. In various embodiments, an ion reflector is positioned in a field-free region to correct the energy of at least one of the first or second group of ions and fragments thereof before they reach the ion detector.

In various embodiments, the mass analyzer comprises a TOF mass analyzer having multiple flight paths, multiple modes of operation that can be performed simultaneously in time, or both. This TOF mass analyzer includes a path selecting ion deflector that directs ions selected from a packet of sample ions entering the mass analyzer along either a first ion path, a second ion path, or a third ion path. In some embodiments, even more ion paths may be employed. In various embodiments, the second ion deflector can be used as a path selecting ion deflector. A time-dependent voltage is applied to the path selecting ion deflector to select among the available ion paths and to allow ions having a mass-to-charge ratio within a predetermined mass-to-charge ratio range to propagate along a selected ion path.

For example, in various embodiments of operation of a TOF mass analyzer having multiple flight paths, a first predetermined voltage is applied to the path selecting ion deflector for a first predetermined time interval that corresponds to a first predetermined mass-to-charge ratio range, thereby causing ions within first mass-to-charge ratio range to propagate along the first ion path. In various embodiments, this first predetermined voltage is zero allowing the ions to continue to propagate along the initial path. A second predetermined voltage is applied to the path selecting ion deflector for a second predetermined time range corresponding to a second predetermined mass-to-charge ratio range thereby causing ions within the second mass-to-charge ratio range to propagate along the second ion path. Additional time ranges and voltages including a third, fourth etc. can be employed to accommodate as many ion paths as are required for a particular measurement. The amplitude and polarity of the first predetermined voltage is chosen to deflect ions into the first ion path, and the amplitude and polarity of the second predetermined voltage is chosen to deflect ions into the second ion path. The first time interval is chosen to correspond to the time during which ions within the first predetermined mass-to-charge ratio range are propagating through the path selecting ion deflector and the second time interval is chosen to correspond to the time during which ions within the second predetermined mass-to-charge ratio range are propagating through the path selecting ion deflector. A first TOF mass separator is positioned to receive the packet of ions within the first mass-to-charge ratio range propagating along the first ion path. The first TOF mass separator separates ions within the first mass-to-charge ratio range according to their masses. A first detector is positioned to receive the first group of ions that are propagating along the first ion path. A second TOF mass separator is positioned to receive the portion of the packet of ions propagating along the second ion path. The second TOF mass separator separates ions within the second mass-to-charge ratio range according to their masses. A second detector is positioned to receive the second group of ions that are propagating along the second ion path. In some embodiments, additional mass separators and detectors including a third, fourth, etc. may be positioned to receive ions directed along the corresponding path. In one embodiment, a third ion path is employed that discards ions within the third predetermined mass range. The first and second mass separators can be any type of mass separator. For example, at least one of the first and the second mass separator can include a field-free drift region, an ion accelerator, an ion fragmentor, or a timed ion selector. The first and second mass separators can also include multiple mass separation devices. In various embodiments, an ion reflector is included and positioned to receive the first group of ions, whereby the ion reflector improves the resolving power of the TOF mass analyzer for the first group of ions. In various embodiments, an ion reflector is included and positioned to receive the second group of ions, whereby the ion reflector improves the resolving power of the TOF mass analyzer for the second group of ions.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

The claims should not be read as limited to the described order or elements unless stated to that effect. While the inventions has been particularly shown and described with reference to specific illustrative embodiments, it should be understood that various changes in form and detail may be made without departing from the scope of the appended claims. By way of example, any of the disclosed features can be combined with any of the other disclosed features to, practice a method of MALDI ion formation or produce a mass analyzer system in accordance with various embodiments of the present teachings. For example, two or more of any of the various disclosed sample handling mechanisms, ion sources, optical systems, ion optical systems, heater systems, temperature-controlled surface configurations, ion optical assemblies, and mass analyzers can be combined to produce a mass analyzer system in accordance with various embodiments of the present teachings. Therefore, all embodiments that come within the scope and spirit of the following claims and equivalents thereto are claimed.

What is claimed is:

1. An ion optical assembly comprising:
a mounting body having a front side and a back side;
a front securing member having a threaded surface and a contact face;
a front member having a threaded opening configured to accept the threaded surface of the front securing member, the front member being attached to the mounting body by at least one attachment member; and
a first plurality of ion optical elements disposed between the front side of the mounting body and the front member,
each ion optical element of the first plurality having a recess structure adapted to receive a complimentary registration structure, a registration structure aligning an ion optical element of the first plurality with respect to at least one other ion optical element of the first plurality when said registration structure is registered in a complimentary recess structure by application of a compressive force by the front securing member against the first plurality of ion optical elements;
wherein the threaded opening of the front member is configured such that when the threaded surface of the front securing member is engaged in the threaded opening of the front member, the contact face of the front securing member can contact an ion optical element of the first plurality and apply a compressive force against the first plurality of ion optical elements.

2. The ion optical assembly of claim 1, further comprising:
a back securing member having a threaded surface and a contact face;
a back member having a threaded opening configured to accept the threaded surface of the back securing member, the back member being attached to the mounting body by at least one attachment member; and
a second plurality of ion optical elements disposed between the back side of the mounting body and the back member,
each ion optical element of the second plurality having a recess structure adapted to receive a complimentary registration structure, a registration structure aligning an ion optical element of the second plurality with respect to at least one other ion optical element of the second plurality when said registration structure is registered in a complimentary recess structure by application of a compressive force by the back securing member against the second plurality of ion optical elements;
wherein the threaded opening of the back member is configured such that when the threaded surface of the back securing member is engaged in the threaded opening of the back member, the contact face of the back securing member can contact an ion optical element of the second plurality and apply a compressive force against the second plurality of ion optical elements.

3. The ion optical assembly of claim 1, wherein the threaded opening comprises one or more of a substantially continuous helical ridge, a substantially continuous spiral ridge, an interrupted helical ridge, an interrupted spiral ridge, and combinations thereof.

4. The ion optical assembly of claim 3, wherein the threaded surface of the front securing member is engaged in the threaded opening of the front member by screwing the front securing member into the threaded opening of the front member.

5. The ion optical assembly of claim 1, wherein the threaded opening comprises one or more of a substantially continuous circular ridge, an interrupted circular ridge, and combinations thereof.

6. The ion optical assembly of claim 5, wherein the threaded surface of the front securing member is engaged in the threaded opening of the front member by pushing the front securing member into the threaded opening of the front member.

7. The ion optical assembly of claim 1, wherein the contact surface of the front securing member is beveled and the ion optical element contacted by the front securing member has a beveled surface adapted to receive said beveled contact surface.

8. The ion optical assembly of claim 1, wherein the front member is attached to the mounting body by three attachment members.

9. The ion optical assembly of claim 1, wherein the at least one attachment members comprises a rod.

10. The ion optical assembly of claim 1, wherein the mounting body comprises a region for performing ion fragmentation.

11. The ion optical assembly of claim 1, wherein the region for performing ion fragmentation comprises a collision cell.

12. The ion optical assembly of claim 1, wherein the front securing member is self locking in the front member upon application of a pre-selected torque.

13. A system for mounting and aligning ion optic components, comprising:
a mounting base having a mounting surface and a back surface opposite the mounting surface, the mounting surface having a plurality of pairs of protrusions protruding from the mounting surface and one or more mounting structures associated with each pair of protrusions;
at least one electrical connection element associated with each pair of protrusions, the connection elements passing through the mounting base from the back surface to the mounting surface;
two or more ion optic component supports, each ion optic component support having a pair of recesses configured to receive one or more of the plurality of pairs of protrusions;
such that when the pair of recesses of an ion optic component support is brought into registration with the corresponding pair of protrusions by mounting an ion optic component to the mounting base using the one or more mounting structures associated with the pair of protrusions, an ion optics component mounted in said ion optic component support is substantially aligned with another ion optics component so mounted and an electrical connection site on said ion optics component is proximate to a corresponding electrical connection element associated with said corresponding pair of protrusions.

14. The system of claim 13, wherein one of the ion optic component supports comprises a mounting body having a region for performing ion fragmentation.

15. The system of claim 14, wherein the region for performing ion fragmentation comprises a collision cell.

16. The system of claim 14, wherein an ion optics assembly is mounted to the mounting body, wherein the ion optics assembly comprises:

a front securing member having a threaded surface and a contact face;

a front member having a threaded opening configured to accept the threaded surface of the front securing member, the front member being attached to the mounting body by at least one attachment member; and a first plurality of ion optical elements disposed between a front side of the mounting body and the front member, each ion optical element of the first plurality having a recess structure adapted to receive a complimentary registration structure, a registration structure aligning an ion optical element of the first plurality with respect to at least one other ion optical element of the first plurality when said registration structure is registered in a complimentary recess structure by application of a compressive force by the front securing member against the first plurality of ion optical elements;

wherein the threaded opening of the front member is configured such that when the threaded surface of the front securing member is engaged in the threaded opening of the front member, the contact face of the front securing member can contact an ion optical element of the first plurality and apply a compressive force against the first plurality of ion optical elements.

17. The system of claim 16, wherein the ion optics assembly comprises:

a back securing member having a threaded surface and a contact face;

a back member having a threaded opening configured to accept the threaded surface of the back securing member, the back member being attached to the mounting body by at least one attachment member; and a second plurality of ion optical elements disposed between a back side of the mounting body and the back member, each ion optical element of the second plurality having a recess structure adapted to receive a complimentary registration structure, a registration structure aligning an ion optical element of the second plurality with respect to at least one other ion optical element of the second plurality when said registration structure is registered in a complimentary recess structure by application of a compressive force by the back securing member against the second plurality of ion optical elements;

wherein the threaded opening of the back member is configured such that when the threaded surface of the back securing member is engaged in the threaded opening of the back member, the contact face of the back securing member can contact an ion optical element of the second plurality and apply a compressive force against the second plurality of ion optical elements.

18. The system of claim 13, wherein the plurality of pairs of protrusions are configured such that only one orientation of an ion optic component support will enable the pair of recesses of the ion optic component support to be brought into registration with the corresponding pair of protrusions.

19. The system of claim 13, wherein the pairs of protrusions are configured to have different shapes for ion optic component supports for different ion optic components.

20. An ion optical assembly comprising:

a mounting body having a front side and a back side, and a region disposed therein for performing ion fragmentation by collision induced dissociation;

a front securing member having a threaded surface and a contact face;

a front member having a threaded opening configured to accept the threaded surface of the front securing member, the front member being attached to the mounting body by at least one attachment member;

a first plurality of ion optical elements disposed between the front side of the mounting body and the front member, each ion optical element of the first plurality having a recess structure adapted to receive a complimentary registration structure, a registration structure aligning an ion optical element of the first plurality with respect to at least one other ion optical element of the first plurality when said registration structure is registered in a complimentary recess structure by application of a compressive force by the front securing member against the first plurality of ion optical elements;

wherein the threaded opening of the front member is configured such that when the threaded surface of the front securing member is engaged in the threaded opening of the front member, the contact face of the front securing member can contact an ion optical element of the first plurality and apply a compressive force against the first plurality of ion optical elements;

a back securing member having a threaded surface and a contact face;

a back member having a threaded opening configured to accept the threaded surface of the back securing member, the back member being attached to the mounting body by at least one attachment member; and a second plurality of ion optical elements disposed between the back side of the mounting body and the back member, each ion optical element of the second plurality having a recess structure adapted to receive a complimentary registration structure, a registration structure aligning an ion optical element of the second plurality with respect to at least one other ion optical element of the second plurality when said registration structure is registered in a complimentary recess structure by application of a compressive force by the back securing member against the second plurality of ion optical elements;

wherein the threaded opening of the back member is configured such that when the threaded surface of the back securing member is engaged in the threaded opening of the back member, the contact face of the back securing member can contact an ion optical element of the second plurality and apply a compressive force against the second plurality of ion optical elements.

* * * * *